United States Patent
Pugh et al.

(10) Patent No.: US 8,524,942 B2
(45) Date of Patent: Sep. 3, 2013

(54) SYNTHESIS OF INIMERS AND HYPERBRANCHED POLYMERS

(75) Inventors: Coleen R. Pugh, Akron, OH (US); Anirudha Singh, Baltimore, MD (US)

(73) Assignee: The University of Akron, Akron, OH (US)

( * ) Notice: Subject to any disclaimer, the term of this patent is extended or adjusted under 35 U.S.C. 154(b) by 636 days.

(21) Appl. No.: 12/444,166

(22) PCT Filed: Oct. 4, 2007

(86) PCT No.: PCT/US2007/021345
§ 371 (c)(1),
(2), (4) Date: Oct. 7, 2010

(87) PCT Pub. No.: WO2008/045299
PCT Pub. Date: Apr. 17, 2008

(65) Prior Publication Data
US 2011/0046334 A1   Feb. 24, 2011

Related U.S. Application Data

(60) Provisional application No. 60/849,415, filed on Oct. 4, 2006.

(51) Int. Cl.
*C07C 69/52* (2006.01)

(52) U.S. Cl.
USPC .......................................................... 560/223

(58) Field of Classification Search
None
See application file for complete search history.

(56) References Cited

U.S. PATENT DOCUMENTS

| | | | |
|---|---|---|---|
| 4,025,450 | A | 5/1977 | Lamberti et al. |
| 5,155,043 | A | 10/1992 | Murakami et al. |
| 6,100,350 | A | 8/2000 | Wilczek et al. |
| 6,107,408 | A | 8/2000 | Quirk et al. |
| 6,156,859 | A | 12/2000 | Langstein et al. |
| 6,177,562 | B1 | 1/2001 | Uggeri et al. |
| 6,812,298 | B2 | 11/2004 | Dvornic et al. |

FOREIGN PATENT DOCUMENTS

EP   1 688 440 A1   8/2006

OTHER PUBLICATIONS

Database Caplus Chemical Abstracts Service, Columbus, Ohio, US; Database Accession No. 2007:847612, Abstract of Pugh et al., Polymer Preprints (American Chemical Society, Division of Polymer Chemistry) (2007), 48(2), 758-759.*

(Continued)

*Primary Examiner* — Karl J Puttlitz
(74) *Attorney, Agent, or Firm* — Renner, Kenner, Greive, Taylor, Bobak & Weber Co., L.P.A.

(57) ABSTRACT

An inimer, and process for making same, having the following formula:

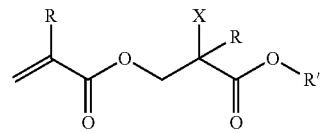

wherein X=halogen, nitroxide, thioester; R=H or $CH_3$; and R'=aliphatic, non-aliphatic, linear or branched, mesogenic, non mesogenic, chiral, achiral, hydrocarbon, non-hydrocarbon, selected from fluorocarbon, oligo(oxyethylene) and siloxane substituents, alkyl, aryl, mesogenic group, non-mesogenic group, aliphatic, non-aliphatic, siloxane, perfluoroalkyl, perfluoroaryl, or other fluorocarbon group, and polymers, and the process of making them, from the inimer.

4 Claims, 5 Drawing Sheets

(56) References Cited

OTHER PUBLICATIONS

Karen L. Wooley, et al., "Influence of shape on the reactivity and properties of dentritic, hyperbranched and linear aromatic polyesters", Polymer, vol. 35, No. 21, 1994, pp. 4489-4495.
Gao, C., et al., "Hyperbranched Polymers: From Synthesis to Applications," Prog. Polym. Sci., 29, 183-275 (2004).
Busson, P., et al., "Preparation of Mesogen-Functionalized Dendrimers for Second-Order Nonlinear Optics," Macromolecules, 35, 1663-1671 (2002).
Sunder, M.F. Quicny, et al., "Hyperbranched Polyether Polyols with Liquid Crystalline properties," Angew. Chem. Int. Ed., 38, 2928-2930 (1999).
Peng, H., et al., "Simple Synthesis, Outstanding Thermal Stability and Optical-Limiting Properties of Functional Hyperbranched Polyarylenes," Macromolecules, 35, 5349-5351 (2002).
Percec, V., "Molecular Design of Novel Liquid Crystalline Polymers with Complex Architecture: Macrocyclics and Dendrimers", Pure Appl. Chem., 67, 2031-2038 (1995).
Kricheldorf, H.R., et al., "New Polymer Syntheses. XCVII. Hyperbranched LC-Polyesters Based on 6-(4-Hydroxyphenyl)propionic Acid and 4-Hydroxybenzoic Acid", J. Polym. Sci., Polym. Chem. Ed., 36, 1397-1405 (1998).
Hawker, C.J., et al., "Preparation of Hyperbranched and Star Polymers by a 'Living,' Self-Condensing Free Radical polymerization," J. Am. Chem. Soc., 117, 10763-10764 (1995).
Frechet, J.M.J., et al., "Self-Condensing Vinyl Polymerization: An Approach to Dendritic Materials," Science, 269, 1080-1083 (1995).
Gaynor, et al., "Synthesis of Branched and Hyperbranched Polystyrenes, "Macromolecules, 29, 1079-1081 (1996).
Weimer, M.W., et al., "Importance of Active-Site Reactivity and Reaction Conditions in the Preparation of Hyperbranced Polymers by Self-Condensing Vinyl Polymerization: Highly Branched vs. Linear Poly[4-(chloromethyl) styrene] by Metal-Catalyzed 'Living' Radical polymerization," J. Polym. Sci., Polym. Chem. Ed., 36, 955-970 (1998).
Ishizu, K., et al., "Kinetics of Hyperbranched Polystyrenes by Free Radical polymerization of Photofunctional Inimer", Macromolecules, 35, 3781-3784 (2002).
Matyjaszewski, K., et al., Preparation of Hyperbranched Polyacrylates by Atom Transfer Radical Polymerization. 1. Acrylic Ab* Monomers in "Living" Radical Polymerizations, Macromolecules, 30, pp. 5192-5194; 2. Kinetics and Mechanism of Chain Growth for the Self-Condensing Vinyl Polymerization of 2-((2-Bromopropionyl)oxy)ethyl Acrylate, pp. 7034-7041; and 3. Effect of Reaction Conditions on the Self-Condensing Vinyl Polymerization of 2-((2-,1997.
Yoo, S.H., et al., "Synthesis of Hyperbranched Polyacrylates in Emulsion by Atom Transfer Radical polymerization," Macromolecules, 35, 1146-1148 (2002).

Ishizu, K., et al., "Synthesis and Characterization of Hyperbranched Poly(ethyl methacrylate) by Quasi-Living Radical Polymerization of a Photofunctional Inimer", Polym. Int., 51, 424-428 (2002).
Lovell, P.A., et al., "Chain Transfer to Polymer in Emulsion Polymerization of n-Butyl Acrylate Studied by 13C NMR Spectroscopy and Gel Permeation Chromatography", Polymer Commun., 32, 98-103 (1991).
Ahmad, N. M., et al., "Chain Transfer to Polymer in Emulsion Polymerization", Macromol. Symp., 143, 231-241 (1999).
Heatley, F., et al., "Chain Transfer to Polymer in Free-Radical Solution Polymerization of 2-Ethylhexyl Acrylate Studied by NMR Spectroscopy", Macromolecules, 34 7636-7641 (2001).
Britton, D.J., et al., Macromol. Symp., 175, 95-104 (2001).
Farook, S.A.M., et al., "Kinetics and Mechanism of Bromine Addition to Derivatives of Unsaturated Aliphatic Carboxylic Acids in Aqueous Solution", Bull. Chem. Soc. Jpn., 57, 1394-1400 (1984).
Mattocks, A.M., et al., "A Synthesis of Serine and Its Methyl Ester", J. Biol. Chem., 165, 501-503 (1946).
Bell, R.P., et al., "Kinetics of the Reactions of Olefins and Halogens in Aqueous Solution. Part III. Reaction of Bromine with Acrylic Acid, Crotonic Acid and Ethyl Acrylate", J. Chem. Soc. (B), 500-503 (1968).
Slieker, L., et al., A Convenient Synthesis of 2S, 3S-Serine-3-D and 2S,3R-Serine-2,3-D2, J. Labelled Compd. Radiopharmaceuticals, 19, 647-657 (1982).
Leibman, K.C., et al., "Synthesis and Properties of Isoserine. A Novel Bromohydrination Method", J. Org. Chem., 27, 438-440 (1962).
Larcheveque, M., et al., "A Simple Preparation of R or S Glycidic Esters; Application to the Synthesis of Enantiomerically Pure a-Hydroxyesters," Tetrahedron Lett., 28, 1993-1996 (1987).
Shimohigashi, Y., et al., "Walden Inversion of Amino Acids. VIII. Stereospecific Synthesis of D-Isoserine and DIsothreonine from L-Serine and L-Threonine", Memoirs Faculty Sci., Kyushu Univ., 11, 217-224 (1978).
Muller, A.H.E., et al., "Molecular Parameters of Hyperbranched Polymers Made by Self-Condensing Vinyl Polymerization. 1. Molecular Weight Distribution," Macromolecules, 30, 7015-7023 (1997).
Yan, D., et al., "Molecular Parameters of Hyperbranched Polymers Made by Self-Condensing Vinyl Polymerization. 2. Degree of Branching," Macromolecules, 30, 7024-7033 (1997).
Litvinenko, G.I., et al., "Molecular Parameters of Hyperbranched Copolymers Obtained by Self-Condensing Vinyl Copolymerization. 1. Equal Rate Constants," Macromolecules, 32, 2410-2419 (1999).
Schon, F., et al., "New Strategy for the Synthesis of Halogen-Free Acrylate Macromonomers by Atom Transfer Radical Polymerization," Macromolecules, 34, 5394-5397 (2001).
Mori, et al., Surface-Grafted Hyperbranched Polymers by Self-Condensing Vinyl (co)Polymerization Via ATRP. Lehrstuhl fur Makromolekular Chemie II and Bayreuther Zentrum fur Kollorde and Grenzflachen Universitat Bayreuth, 2003, pg. 1-2.

* cited by examiner 0.69 Three-arm ••••••••••
0.55 Comb – – – – –·
0.52 Six-arm + – – +
0.43 Hyperbranched — — —

SYNTHESIS OF INIMERS AND HYPERBRANCHED POLYMERS

The present application claims the benefit of U.S. Provisional Patent Application 60/849,415, filed on Oct. 4, 2006, and entitled "SYSTHESIS OF INIMERS AND HYPERBRANCHED POLYMERS BASED ON 2-HALO-3-HYDROXYLPROPRIONIC ACID, 2-HALO-3-HYDROXYLBUTYRIC ACID, AND THEIR DERIVATIVES", which is incorporated herein by reference in their entireties The present invention was made in the course of research that was supported by National Science Foundation (NSF) Grant DMR 0322338. The United States government may have certain rights to the invention or inventions herein.

BACKGROUND OF THE INVENTION

This invention relates to the synthesis of functional poly(meth)acrylates, particularly hyperbranched poly(meth)acrylates, from their corresponding inimers. These inimers and precursor esters are synthesized from halohydrins.

The effect of different architectures on the chemical and physical properties of the polymers have been an area of research for many years, including of poly(meth)acrylates, which are of commercial and academic interest. Varieties of architectures like linear, star, graft, cyclic, dendritic and hyperbranched poly(meth)acrylates have been synthesized and their physical properties are under investigation.

Halohydrins are typically synthesized by either direct hydrohalogention of the corresponding olefin, or by the first converting the olefin to an epoxide, followed by reaction with HX (HCl/HBr). Ring-opening of glycidic esters with HCl and HBr generates the wrong regioisomer (Kuroyan et. al. and Talasbaeva et al.), with —OH alpha to the ester. Hydrobromination of methacrylates produces a mixture of regioisomers (Farook et. al.). Hydrobromination of acrylates also produces primarily the wrong regioisomer (Slicker et. al.) in low yield due to the formation of a large amount of dibromide as side product (Bell et. al.), although the products were initially assumed to be 2-bromo-3-hyroxypropionate (Mattocks et. al.); the amount of dibromide can be reduced by adding $AgNO_3$ to precipitate AgBr out of the reaction mixture (Leibman et. al.). We have found a much cleaner reaction is to convert the amine group of serine and its ester to a halogen group by diazotization in the presence of KX (Br/Cl) as shown in Scheme 5 (Larchevêque et. al. and Shimohigashi et. al.). The short alkyl esters of serine are either commercially available as HCl salts or are easily synthesized by acid-catalyzed esterification using the desired alcohol as solvent.

Chemically similar polymers having different molecular architecture can exhibit various interesting properties that are different than the polymers of conventional architectures (like linear and branched, cross-linked polymers). Most importantly and distinctly, shear thinning behavior and lower viscosity of these polymers give processing advantages compared to the linear counterparts. This new class of architecture mainly consists of dendrimers and hyperbranched polymers. In contrast to dendrimers, which have uniform distribution of branches in three dimensions, hyperbranched polymers are characterized by random and non-uniform branching. It has been suggested in the reported literatures that dendrimers can successfully be employed in certain applications to achieve improved properties, especially processing properties. Due to lack of entanglements of the chains, the viscosity of these polymers is lower than that of linear polymers. These polymers also have reactive end groups that can be modified and used advantageously in coating and additive applications.

Dendrimers are monodisperse (typically have polydispersity 1.02 or less) (reference: U.S. Pat. No. 6,812,298 B2) and synthesized with controlled step-growth reactions with tedious protection-deprotection strategies and purification. In contrast, hyperbranched polymers are made from one-step, one-pot reactions and are polydisperse. This facilitates the synthesis of a large amount of polymers with higher yield at comparatively lower cost. Due to its imperfect branching and higher polydispersity, the properties of hyperbranched polymers lie between those of dendrimers and linear polymers. This wide window of properties between these of the two extreme architectures makes hyperbranched polymers a potential competitor superior to dendrimers in certain applications.

Until now, the synthetic techniques used to prepare hyperbranched polymers could be divided into two major categories. The first category contains techniques of the single-monomer methodology in which hyperbranched polymers are synthesized by the polymerization of an $AB_n$ monomer. This method also includes self condensing vinyl polymerization (SCVP). The other category contains methods of the double-monomer methodology in which two types of monomers or a monomer pair generates hyperbranched polymers. (C. Guo, D. yan; *Prog. Polym. Sci.* 29 (2004), 183-275.)

Fréchet and co-workers proposed SCVP in which a vinyl monomer can be self-polymerized if it has a pendant group that can be transformed into an initiating site by the action of external stimulus (Fréchet et. al., *Science*, 1995, 269, 1080-1083). Since there are two polymerizing growth sites (vinylic and initiating) and the activities of these sites may differ with each other, the degree of branching (DB) (which is defined as the number of branch units present in the architecture with respect to the total number of different structural units) will have different values for the different systems and/or at different conditions below a theoretical maximum value (DB=0.465); (this value was obtained by theoretical calculations done by Müller et. al., *Macromolecules* 1997, 30, 7024-7033.) detailed theoretical investigations for the hyperbranched polymers have been done by Müller and co-workers. Hyperbranched polymers obtained by SCVP generally have broad molecular weight distribution and any side reaction may lead to cross-linking during synthesis of these polymers. Living polymerizations like atom transfer radical polymerization and group transfer polymerization (GTP) are employed to better control the architecture of these polymers. Numerous styrene and (meth)acrylate based monomers and inimers have been synthesized to produce hyperbranched polymers using the concept of SCVP and living radical polymerization.

Linear poly(meth)acrylates with free ester side chains of different functional groups can be synthesized but hyperbranched structure using SCVP of inimer having different functional groups have not been synthesized yet. As an example: although numerous dendrimers and hyperbranched polyacrylates (Busson et. al., Sunder et. al., Peng et. al., Percec and Kricheldorf et. al.) have been synthesized with the mesogens (compounds that under suitable conditions of temperature, pressure, and concentration can exhibit a liquid crystal phase) are attached only at their periphery, or within the main chain of the polymer, none have been synthesized with the mesogens attached as a side chain throughout the branched structure.

In addition, the hyperbranched polyacrylates and poly(meth)acrylates synthesized by homopolymerization of an inimer were not analogs of linear poly(meth)acrylates. In contrast, the first hyperbranched polystyrene (Hawker et. al.) produced by SCVP (Fréchet et al.) of an inimer by a radical mechanism produced a hyperbranched polymer that is fairly analogous to linear polystyrene (but with an extra —$CH_2O$—) (Scheme 1).

Scheme 1: Hyperbranched polystyrene

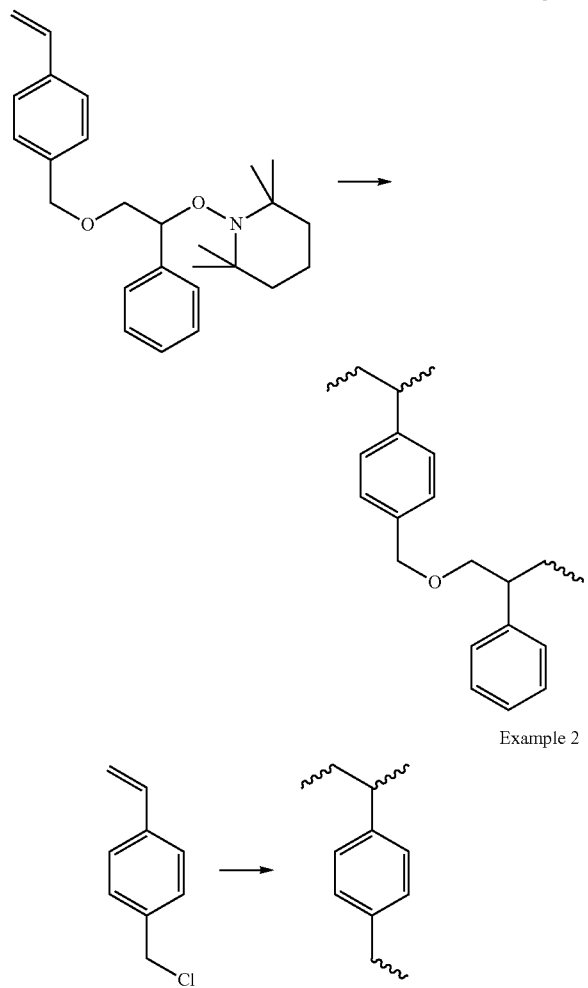

Example 1

Example 2

Subsequently synthesized "hyperbranched polystyrenes" (Gaynor et. al., Weimer et. al., Ishizu et. al.) such as the second example in Scheme 1, incorporate the aromatic ring within the main chain of the polymer and therefore more analogous to polymers produced by step polymerizations; in addition, all free aromatic groups not incorporated into branches are functionalized with an initiator fragment. Similarly, all of the hyperbranched poly(meth)acrylates (Matyjaszewski et. al. and Yoo. et. al.) synthesized to date by SCVP incorporate the alkyl ester into the polymer backbone upon branching (Scheme 2), and leave an alkyl ester side chain functionalized with an initiator fragment at incomplete branching. These polymers are therefore not analogs of linear poly(meth)acrylates, whose properties could be compared to determine architectural effects. They are also not analogs of the branched poly(meth)acrylates produced in conventional radical polymerizations in which branching occurs by chain transfer at a site along the polymer backbone, rather than at the ester side chains.

Scheme 2: "Hyperbranched" poly(meth)acrylates reported in literatures

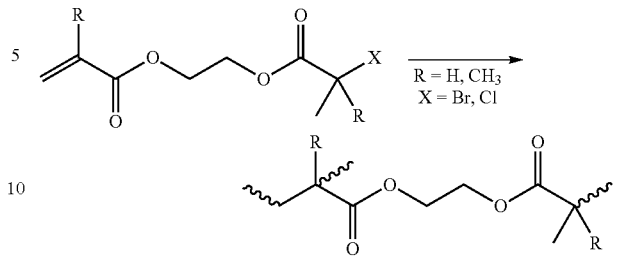

This method synthesizes the first hyperbranched analogs of the linear poly(meth)acrylates from the corresponding inimers based on a halohydrin (bromoydrin/chlorohydrin) intermediate. The detailed description of which is given in the subsequent sections.

SUMMARY OF THE INVENTION

The present invention is directed to the synthesis of inimers and hyper branched polymers based on, e.g., 2-halo-3-hydroxypropionic acid, 2-halo-3-hydroxybutyric acid and their derivatives. Polyacrylates synthesized in accordance with the present in invention can have different functional groups attached as free ester chains. Polyacrylates, an important class of polymer, are used in a variety of applications, and by having different functional groups can provide utility as, for example, ingredients in paints, coatings, textiles, adhesives, superabsorbent materials, contact lenses, display devices, polyelectrolytes & hydrogels. The architectural effects on the physical properties of polyacrylates will provide benefits and increase performance for a number of applications for such polymers.

The polyacrylates are achieved by using the inimers (an inimer contains an initiating site and polymerizable group in the same molecule) of the present invention that have been synthesized from a key halohydrin based intermediate. This intermediate chemical is synthesized from serine using a diazotization synthetic route. Polymerization of these inimers result in functional hyperbranched poly(meth)acrylates. For the purpose of this application, poly(meth)acrylates indicates polyacrylates and polymethacrylates, including poly(methyl acrylate) and poly(methyl methacrylate) and their derivatives. The polymers can be made by using self-condensing vinyl polymerization (SCVP) and radical polymerization, such as, for example: atom transfer radical polymerization. These hyperbranched polyacrylates contain an ester group attached to every carbon atom along the polymer backbone, with a non-initiator-containing alkyl ester attached as a free side chain. The architecture of these polymers is more chemically analogous to linear polyacrylates.

This invention provides greater flexibility of making different variety of hyperbranched functional polyacrylates in a single pot, single step reaction and facilitates achieving a number of physical properties due to architectural differences of the polymers. The ester substituents can be formed from any alcohol, and therefore includes aliphatic or non-aliphatic, linear or branched, mesogenic or non-mesogenic, chiral or achiral, and hydrocarbon or non-hydrocarbon (such as fluorocarbon, oligo(oxyethylene), and siloxane) substituents.

BRIEF DESCRIPTION OF THE DRAWINGS

The foregoing and other features and advantages of the present invent: on will become apparent to those skilled in the art to which the present invention relates upon reading the following description with reference to the accompanying drawings, in which.

DETAILED DESCRIPTION OF THE INVENTION

Figure 1:
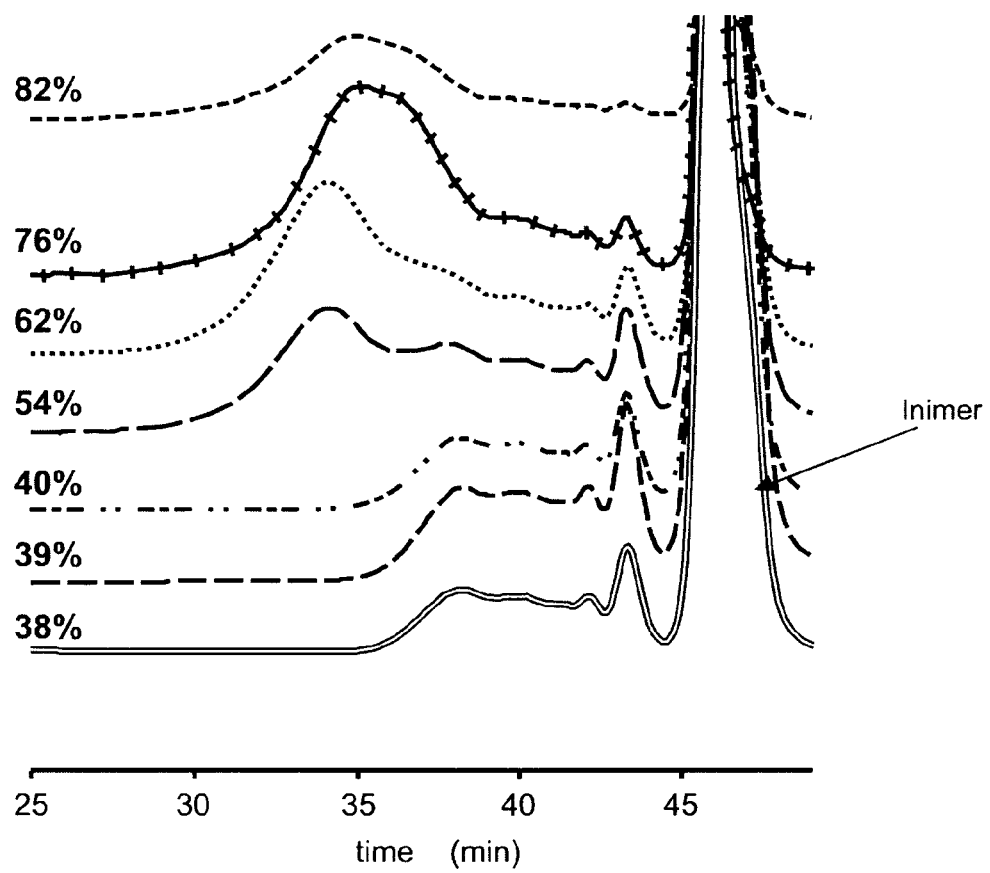
FIG. 1 shows variation of molecular weight and its distribution with conversion during polymerization of mesogenic inimer.

The present invention is directed to the synthesis of hyperbranched functional poly(meth)acrylates by self-condensing vinyl polymerization or SCVP of the corresponding inimers, which are synthesized from 2-halo-3-hydroxypropionate and 2-halo-3-hydroxybutyrate derivatives. This invention synthesizes the first hyperbranched analogs of linear poly(meth)acrylates, including those of the conventional monomers such as methyl, using inimers, which produce a polymer with an ester group attached to every other carbon along the polymer backbone, with a non-functionalized alkyl ester attached as a free side chain.

The present invention synthesizes the inimer from halohydrin (eg: bromohydrin), in higher yields by converting the amine group of serine or its derivatives into halogen by diazotization reaction in the presence of halogen-containing salts (eg: KBr). For the purpose of this application, an "inimer" is a molecule having a vinyl group and an initiating group which will initiate polymerization of the molecule. This step was followed by esterification of the alcohol of the desired functional group required in the polymer. This hydroxy group containing ester was further esterified with acryloyl chloride or acrylic anhydride using triethylamine as a reagent. In the case of bromohydrin-based esters, acrylic anhydride was used for the esterification to avoid any halogen-exchange of the halogen group (Br to Cl), which occurred when acryloyl chloride was used in esterification and this was confirmed with electron ionization mass-spectroscopy and $^{13}$C-NMR spectroscopy. During the polymerization of the inimer by ATRP, decomposition of the inimer was confirmed by $^1$H-NMR and $^{13}$C-NMR spectroscopy and occurred when free ligand (not complexed with the copper catalyst) of the higher basicity such as N,N,N',N'-pentamethyldiethylenetriamine (PMDETA) was present in the reaction system. This was avoided by performing a catalyst-ligand complex first and subsequently adding the inimer into the reaction mixture. This decomposition also did not occur if a ligand of low basicity (2,2'-dipyidine) was used.

The present invention synthesizes hyperbranched polymers using ATRP of the inimers by SCVP and by self-condensing vinyl copolymerization (SCVCP) (in which inimer and monomer are copolymerized together). Theoretical calculations of the different structural features of the architecture are available in the literature and we have obtained the qualitative information about the branching of hyperbranched architecture. Detailed analysis of the poly(methyl acrylate) by $^1$H, $^{13}$C and $^1$H—$^{13}$C HSQC NMR spectroscopy provided us information about branching. GPC, light scattering and solution viscosity molecular weight data further confirmed the existence of the hyperbranched structure. Poly(methyl acrylate) was synthesized, as was more complex molecular systems like poly(mesogenic acrylate), poly(perfluoro acrylate) and poly(dodecyl acrylate).

Detailed NMR analysis of the hyperbranched mesogenic polyacrylate by $^1$H, $^{13}$C, $^1$H—$^{13}$C Heteronuclear Single Quantum Correlation (HSQC), $^1$H—$^{13}$C Heteronuclear Multiple Bond Correlation (HMBC) & TOtal Correlation Spectroscopy (TOCSY) was performed to obtain the branch points in the hyperbranched mesogenic polyacrylate. Gel Permeation Chromatography (GPC) molecular weights relative to polystyrene standards aid absolute molecular weights (by light scattering) and solution viscosity molecular weigh data further confirmed the existence of the hyperbranched structure. Contraction factors (ratio of mean square radius of gyration of branched polymer to that of linear polymer) of different architectures (Three-arm, Six-arm, Comb and Hyperbranched) for mesogenic polyacrylates were obtained and compared. Detailed procedure for synthesis & studies of physical properties of Linear, Three-arm, Comb and Six-arm mesogenic polyacrylates are described in various research publications, such as ((i). Kasko, M. A.; Heintz, M. A.; Pugh, C. *Macromolecules* 1998, 31, 256-271, (ii) Chang, C.; Pugh, C. *Macromolecules* 2001, 34, 2027-2039, (iii) Kasko, M. A.; Pugh, C. *Macromolecules* 2004, 37, 4993-50C1, and (iv) Kasko, M. A.; Pugh, C. *Macromolecules* 2006, 39, 6800-6810.). Results supported the fact that the structure becomes more compact as the branching in the polymers is increased. Intrinsic viscosity of the hyperbranched polymer is also lower compared to its linear counterpart, and at a particular molecular weight, intrinsic viscosity decreases as branching increases (Linear>Three-arm>Comb/Six-arm>Hyperbranched). Isotropization temperature of hyperbranched mesogenic polyacrylate is also lower compared to its linear cc unterpart with broader phase transitions.

Numerous dendrimers and hyperbranched polymers have been synthesized with the mesogens attached only at the periphery, or within the main-chain of the polymer but unlike our's mesogenic hyperbranched polyacrylates, none have been synthesized with the mesogen attached as a side chain throughout the branched structure. The present invention makes it possible to produce hyperbranched polymers having different ester substituents, which can be used in different applications having the benefit of both the architecture and the free ester group present in the polymer. Mesogenic polyacrylate was synthesized for liquid crystalline applications where lower viscosity of the hyperbranched polymer potentially and advantageously can be used in the liquid crystalline display devices. Alkyl and perfluoro ester group containing polyacrylates could potentially be used in the adhesive and coating applications. Siloxane and oligo-oxyethylene ester substituents containing hyperbranched polyacrylates could be used in contact lenses and water based adhesives/cosmetics, respectively. Hyperbranched polyacrylic acid and its different salts could also be prepared for superabsorbent materials and polyelectrolytes. The flexibility of attaching any kind of free ester side group in the inimers and hence in the hyperbranched polyacrylates broadens the area of application of these hyperbranched polyacrylates.

The present invention is directed to a process to synthesize hyperbranched functional poly(meth)acrylates by SCVP and SCVCP of the corresponding inimers, which are synthesized from halohydrins and their derivatives. The invention synthesizes the first hyperbranched analogs of linear poly(meth)acrylates, including those of the conventional monomers such as methyl, mesogenic and dodecyl using $2^{nd}$ type of inimers shown in Scheme 3, which produce a polymer with an ester group attached to every other carbon along the polymer backbone, with a non-functionalized alkyl ester attached as a free side chain unlike those synthesized to date by SCVP, which incorporate alkyl ester into the polymer backbone upon branching (Scheme 3), and leave an alkyl ester side chain functionalized with an initiator fragment at incomplete branching. The halogen group could be reduced to obtain a polymer without any initiator containing side chains in the polymer.

Scheme 3: Our "Hyperbranched" poly(meth)acrylates

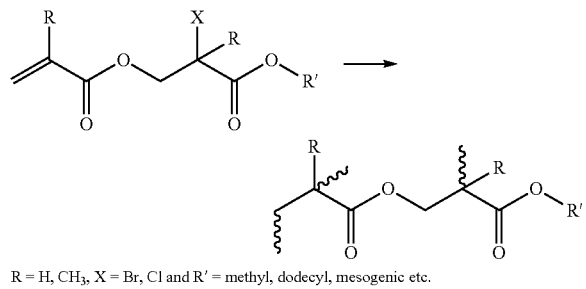

R = H, CH₃, X = Br, Cl and R' = methyl, dodecyl, mesogenic etc.

This new type of inimer will give hyperbranched polymers that are true analogs of the linear polyacrylates. As shown in Scheme 4 (examples), the key intermediate for the inimer is a halohydrin (bromohydrin/chlorohydrin). These inimers are prepared from the esterification of the ester of halohydrins.

Scheme 4: Synthesis of inimers

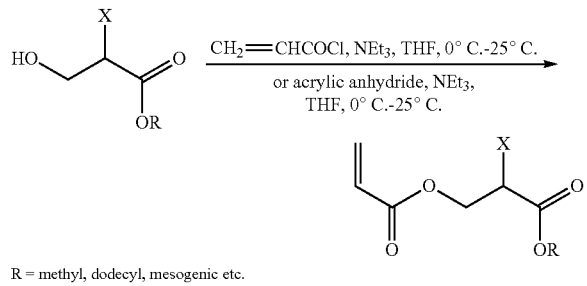

R = methyl, dodecyl, mesogenic etc.

Scheme 5: Synthesis of halohydrin

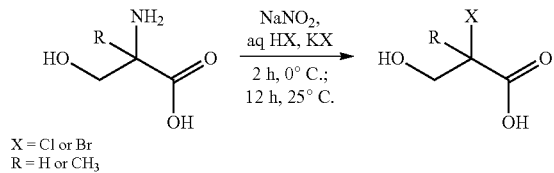

X = Cl or Br
R = H or CH₃

As an example, 2-chloro-3-hydroxypropionic acid (chlorohydrin) was synthesized from acidic aqueous solution (HCl) of (DL)-2-amino-3-hydroxy-propionic acid (DL-serine) (R=H) in the presence of KCl with yield ~60%.

This reaction is important to introduce initiating group in the final inimer, which will act as initiating group during polymerization.

This step was followed by esterification of the alcohol of the desired functional group required in the polymer. This step requires an acid-catalyzed esterification method that can be done in the presence of the solvent or in the bulk. The alcohol (ROH) can be used in slight excess, in equimolar amount or in large excess to produce the ester in moderate to higher yields (Scheme 5). As an example: 2-chloro-3-hydroxypropionic acid was reacted with a large excess of methanol in the presence of a catalytic amount of HCl at moderate temperatures to produce methyl-2-chloro-3-hydroxypropionate. Moderate temperature was used to avoid any formation of the side product which can be resulting from the self-esterification of the 2-chloro-3-hydroxypropionic acid.

Scheme 6: Synthesis of 2-chloro-3-hydroxypropionates

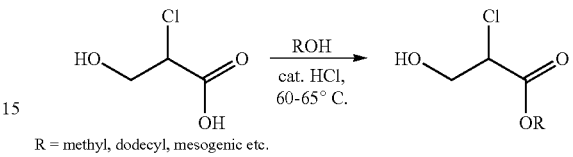

R = methyl, dodecyl, mesogenic etc.

This step incorporates a functional group in the final inimer and this functional group acts as a free ester pendant group in the polymer.

The hydroxy group obtained in the last step was further esterified with acryloyl chloride or acrylic anhydride using triethylamine as a reagent to get the imime (Scheme 4). This step incorporates vinylic group in the inimer which acts as a monomeric site in the polymerization.

In case of bromohydrin-based esters, acrylic anhydride was used for the esterification to avoid any halogen-exchange of the bromine group, which occurred when acryloyl chloride was used in esterification as confirmed with electron-ionization mass spectroscopy and ¹³C-NMR spectroscopy. When acryloyl chloride was used, a mixture of inimers having Br and Cl initiating groups was obtained.

A side product as impurity was obtained during the synthesis of the inimer having Cl as initiating group (but not with Br as initiating group). The yield of the product varied with the type of the functional group present in the precursor ester.

These synthesized inimers having vinylic monomeric site and initiating site both in the same molecule, which upon polymerization produce hyperbranched polymer containing branches upon branches (Scheme 7 for an example). This inimer can be polymerized or copolymerized with the monomer to obtain hyperbranched polymers.

Scheme 7: Synthesis of hyperbranched polymers by SCVP of inimers

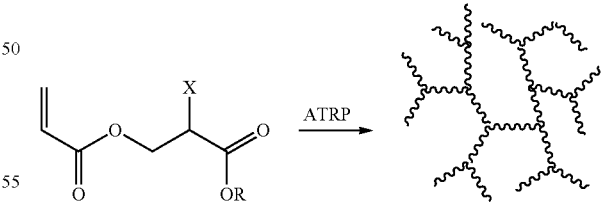

We have used ATRP to obtain these polymers as these provide better control and living nature of the polymerization can be maintained. By this technique we re able to make hyperbranched polyacrylates that have many halogenated chain end groups and functional groups attached as pendant groups. The halogenated chain end groups can be modified to other groups and advantageously used for different applications. A skill worker or an expert can synthesize an inimer with a functional group suitable for other living polymerization.

An ideal dendrimer contains only fully branched repeating units without any linearly repeating units, and an ideal linear polymer contains only linear repeating units, without any branches; in contrast a hyperbranched polymer contains a mixture of linear and fully branched repeat units. The degree of branching (DB), which is defined as the number of branched units relative to the total number of the units (includes linear, branched and terminal units). For an ideal dendrimer this value is 1 and for linear polymer it is 0. For a hyperbranched polymer it is greater than zero and less than 1, with typical values being from about 0.25 to 0.45. (U.S. Pat. No. 6,812,298 B2)

Unlike ideal dendrimers, which have a polydispersity of ~1, hyperbranched polymers have a polydispersity that increases as conversion increases. The polydispersities can become more than 1.1 even at low conversions and can drastically increase with increasing conversion. As the different hyperbranched polymer molecules can combine to give higher molecular weight polymer, the value of polydispersity can increase exponentially as conversion increases. So, for higher conversion the typical value of polydispersity can exceeds 2.0 even when controlled radical polymerization is used. Various authors have compiled data showing various polydispersity values of the hyperbranched polymer synthesized. These differences between the polydispersities and degree of branching of hyperbranched polymers versus dendrimers are indicative of the higher non-ideality, randomness and irregularity of hyperbranched polymers compared to dendrimers. Table 1 shows the results for the different functional hyperbranched polyacrylates, which further confirms the formation of hyperbranched architecture. A variety of inimers containing different ester substituents were synthesized including, methyl, pefluoro, mesogenic, dodecyl, oligo-oxyethylene and siloxane containing ester substituents.

analysis by NMR is required. $^1$H & $^{13}$C NMR spectra of these hyperbranched polymers are very similar to corresponding NMR spectra of inimers and linear polymers. Several overlapped resonances limit the possibility of separate resonances for branched structure. More distinct and less overlapped resonances were obtained after reduction of —Cl end groups into —H in the mesogenic hyperbranched polymer. HSQC, HMBC and TOCSY experiments were performed for the qualitative analysis of the hyperbranched structure. Quantitative analysis is possible but difficult assuming errors in the calculated values of reactivity ratio and degree of branching.

Figure 3:
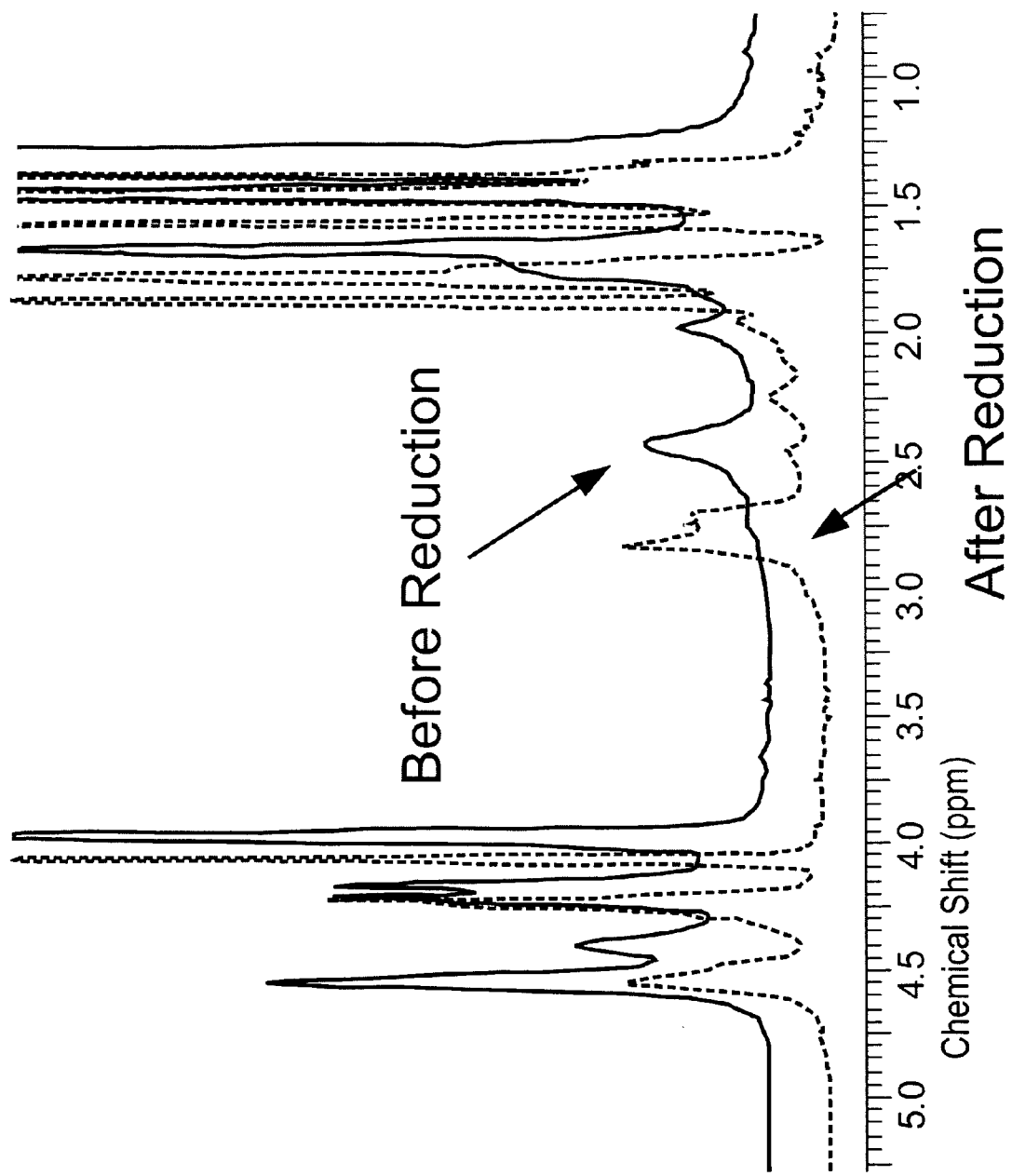
FIG. 3 is a graph of $^1$H NMR spectrum of hyperbranched mesogenic polyacrylate before and after reduction.
Figure 3:
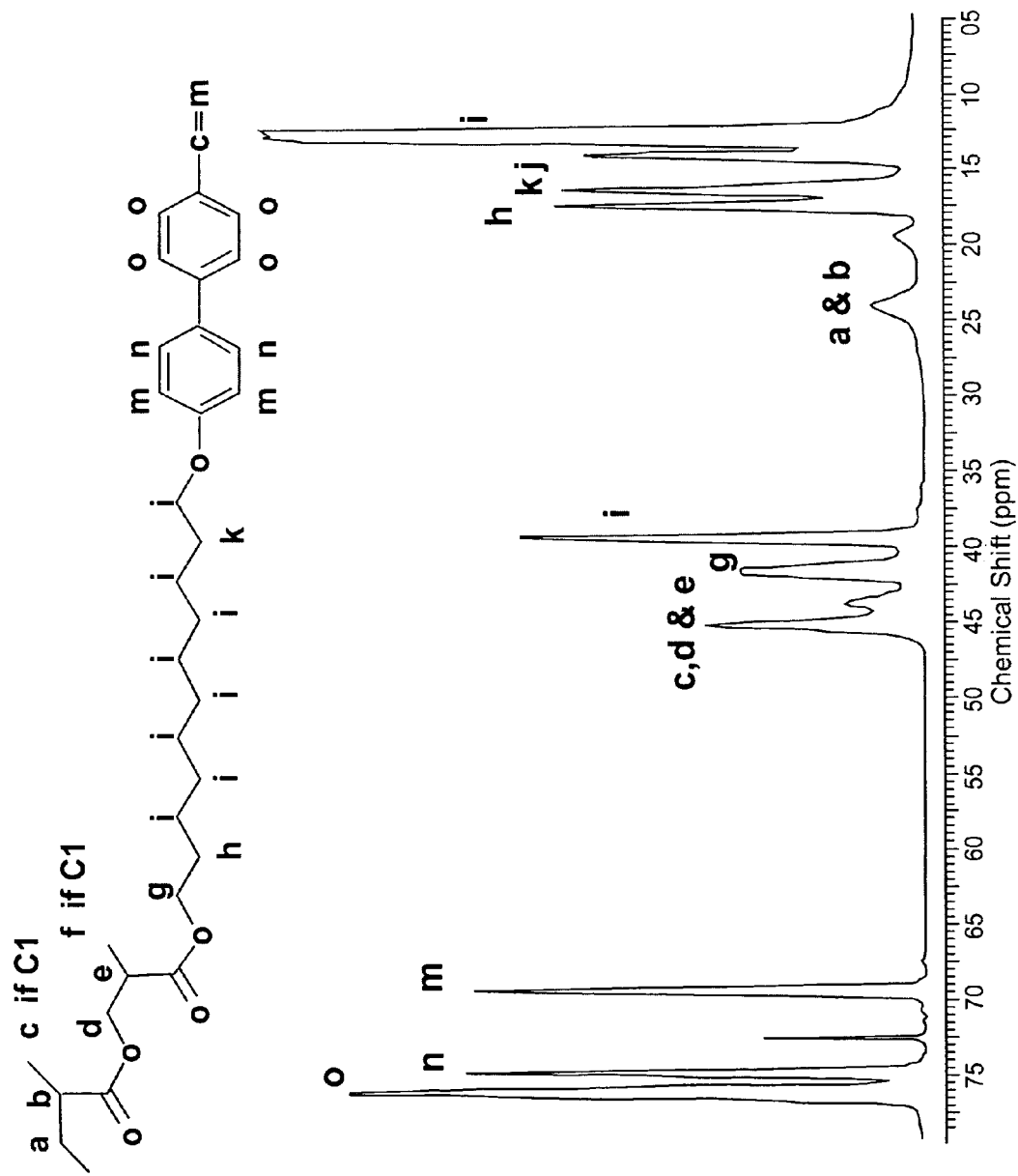

FIG. 3 shows $^1$H-NMR before reduction and after reduction of the —Cl end groups into —H groups. The backbone region of the polymer (1-3 ppm) is very broad, indistinct and overlapped. When reduced, some more peaks appeared and they are comparatively less overlapped. The resonance at ~2.8 ppm is assigned for methylene protons alpha to —OCH$_2$. Adjacent to this resonance at ~2.7 ppm is methine proton alpha to —OCH$_2$. This resonance was broad and overlapped in the original polymer. $^{13}$C NMRs of original and reduced polymer are also shown, noticeable changes in the carobonyl region, 165-180 ppm and in the backbone region 30-35 ppm were observed. Detailed analysis by HSQC, HMBC and TOCSY enable us to assign the resonances of different carbons and protons present in the hyperbranched polymer. TOCSY clearly showed that —OCH$_2$ protons are related to —CH proton and these are further related to —CH$_2$ of the backbone. This relationship is due to branching present in the hyperbranched polymer as initiating site has reacted to another vinylic site and produces branching in the polymer. The resonance at ~2.7 ppm is still overlapped but can be used for quantitative analysis of inimer polymerization as it is direct evidence of branching, though with errors associated with curve fitting of this peak. $^1$H NMR analysis shows the

TABLE 1

Molecular weight data for different hyperbranched polyacrylates ($^a$Cl).

| Sample | $^b$Yield | GPC$_{PSt}$ | | GPC$_{LS}$ | | Solution Viscosity | |
|---|---|---|---|---|---|---|---|
| | | M$_w$ | Pdi | M$_w$ | Pdi | M$_v$ | Pdi |
| $^c$Methyl | 40% | 1.76 × 10$^4$ | 1.52 | 21.2 × 10$^4$ | 1.97 | 21.1 × 10$^4$ | 2.19 |
| $^d$Mesogenic | 66% | 3.26 × 10$^4$ | 1.90 | 11.6 × 10$^4$ | 2.49 | 11.1 × 10$^4$ | 2.75 |
| $^e$Dodecyl | 30% | 2.07 × 10$^4$ | 2.13 | 2.03 × 10$^4$ | 1.80 | 2.07 × 10$^4$ | 2.40 |
| $^f$Perfluoro | 22% | 11.9 × 10$^4$ | 2.39 | 23.9 × 10$^4$ | 1.93 | NA | |

$^a$Initiating group in the inimer.
$^b$Gravimetrical yield after several precipitations.
$^c$Inimer/Cu(I)Cl/Me$_6$TREN (50/1/1) in water (inimer/water 50:50 w/v) at 50° C. for 44 h, 53% conversion by $^1$H-NMR.
$^d$Inimer/Cu(I)Cl/Me$_6$TREN (30/1/1.2) in a mixed solvent water/acetonitrile (16.6% of water) (inimer/solvent 30:70 w/v) at 90° C. for 120 h, ~80% conversion by $^1$H-NMR.
$^e$Inimer/Cu(I)Br/PMDETA (50/1/1.2) in anisole (inimer/anisole 50:50 w/v) at 130° C. for 18 h, 60% conversion by $^1$H-NMR.
$^f$Inimer/Cu(I)Cl/2,2'-bipyridine (43/1/1.5) in toluene (inimer/toluene 50:50 w/v) at 90° C. for 6 h, 36% conversion by $^1$H-NMR(only in CDCl$_3$). GPC$_{PSt}$ & GPC$_{LS}$ experiments were carried out in Trichlorobenzene (TCB) as a solvent.

SEC traces clearly showed formation of oligomers and as conversion increased molecular weight increased with broader distribution. At the early stage of conversion, smaller oligomers were prominent and higher molecular weight polymers were obtained at higher conversion. The statistical nature of inimer polymerization results in formation of oligomers and growth of polymer chain occurs by its addition to an inimer or oligomers resulting polymers with broader polydispersity index. Results obtained by SEC are consistent with statistical nature of inimer polymerization by SCVP technique.

To get the reactivity ratio and degree of branching values for the inimer polymerization, qualitative and quantitative meth-mesogenic polyacrylate has a broad resonance at ~2.5 ppm appears only due to methine protons alpha to —OCH$_2$ and that is coming from branch points. The presence of branching can also be related to the GPC traces obtained at various conversions during the polymerization. The broad molecular weight distribution with different oligomers, FIG. 1 is an outcome of statistical nature of polymerization of the inimer. The contraction factor and intrinsic viscosity (FIG. 2 and FIG. 4) data also supported the formation of branched structures during polymerization of the inimer.

As mentioned above inimer can be hompolymerized using SCVP or cm be co-polymerized with its corresponding monomer resulting in hyperbranched polymers. Since there are two polymerizing growth sites (vinylic and initiating) and the activities of these sites may differ, the degree of branching (DB) will have different values for the different systems and/or under different conditions below a theoretical maximum value ($\overline{DB}$=0.465) (Müller et. al).

For our hyperbranched polymers, we have used modified mathematical definition given by Müller et. al. in which the degree of branching is expressed mathematically according to eq. 1.

$$DB = \frac{\text{(Number of branched units)} + \text{(number of terminal units)} - 1}{\text{(Total number of units)} - 1}. \quad \text{eq. 1}$$

Detailed theoretical investigations have been done by Müller et. al. and to define and obtain values of the structural parameters some assumptions are made such as: the reactivity of the initiating site and vinylic sites are constant throughout the polymerization. There is no cyclic polymer formation. No other side reaction occurs. While comparing theoretical and experimental values of the different parameters, deviation from the predicted values is expected.

As discussed earlier, hyperbranched polymers obtained by this method generally have broad molecular weight distributions and any side reaction may lead to cross-linking. Optimization of the synthetic conditions for obtaining soluble polymer is required and these conditions may vary for different inimers. Living polymerizations like atom transfer radical polymerization and group transfer polymerization (GTP) are employed to get more control on the architecture of these polymers. ATRP was used to synthesize hyperbranched polyacrylates.

SCVP of inimer can be designated as AB* in which B* is a group capable of initiating the polymerization of vinyl groups, A. The chain initiation is the addition of an initiating B* group to the vinyl group of another monomer forming a dimer with two active sites and one double bond. Both the initiating center, B*, and the newly created propagating center, A* can, react with the vinyl group of another molecule (monomer or polymer) in the same way with rate constants, $k_b$ and $k_a$, respectively.

Example

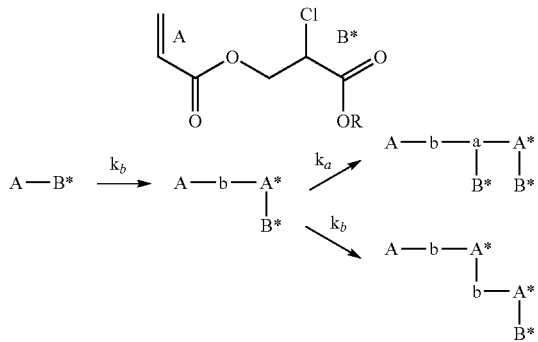

In SCVP reactivities of initiating and propagating centers, A* and B* are generally different from each other. If the reactivity of one of these two sites is very large compared to other site a linear polymer is obtained. A reactivity ratio r ($r=k_a/k_b$) is defined, which is a mathematical representation of the relative reactivities of these sites (A* and B*) and degree of branching (DB) in a polymerizing system (inimer and polymer both together) is defined as (Müller et. al):

$$\overline{DB} = \frac{2B}{1 - M - 2A'}$$

in which,
$\overline{DB}$ is average degree of branching
B is fraction of branch points
M is fraction of monomer
A' is fraction of vinyl group for polymer only.

$$r = \frac{1 - x - B^*}{1 - \ln B^* - B^*}$$

In Which,
x is conversion of A groups (vinylic group)
B* is fraction of initiating centers (reactive B groups)

During the polymerization by ATRP, decomposition of the inimer, which was confirmed by $^1$H-NMR and $^{13}$C-NMR spectroscopy, occurred when free ligand (not complexed with the copper catalyst) of the higher basicity (PMDETA) was present in the reaction system. This was avoided by performing catalyst-ligand complex and subsequently adding inimer into the reaction mixture. This decomposition also did not occur if a less basic ligand (2,2'-bipyridine) was used. Example: When (2-chloro-2-methoxycarbonyl)ethyl propenoate (0.016 g, 0.820 mmol) was taken with PMDETA (1.70 µL, 0.008 mmol) in a vial and $^1$H-NMR was taken after 2.5 h and after 48 h. Extra resonances in $^1$H-NMR spectrum were obtained which indicated occurrence of some reaction of the inimer with the PMDETA. When Cu(I)Cl and PMDETA were allowed to complex first and kept with inimer, no changes in the spectrum were observed even after 48 h.

This decomposition of the inimer in the presence of the free ligand in the polymerization mixture did not occur when 2,2'-bipyridine was used in place of PMDETA (2,2'-bipyridine has lower basicity than PMDETA).

ATRP of inimers having Cl as initiating group are slower when Cu(I)Cl is used as an ATRP catalyst. It is not easy to generate sufficient number of radicals and to obtain significant amount of polymer until we used Me$_6$TREN as ligand which is more efficient ligand than PMDETA or 2,2'-bipyridine. There are several possibilities available to change the reaction conditions and the catalyst/ligand system in different solvents. Different polymerization conditions have been used for the different inimers. Soluble polymer from methyl-inimer (2-chloro-2-methoxycarbonyl)ethyl propenoate can be synthesized using Cu(I)Cl/Me$_6$TREN in water at 50° C. in hour time scale, but when methyl-inimer with Br initiating group (2-bromo-2-methoxycarbonyl)ethyl propenoate was polymerized using Cu(I)Br/Me$_6$TREN in water at 50° C., within 10 min, mainly cross-linked polymer was obtained with some soluble in THF. When mesogenic inimer with Cl initiating group was polymerized using Cu(I)Br/PMDETA, significant amount of the polymer was obtained compared to the polymer that was obtained using Cu(I)Cl/PMDETA for the same reaction time. For the different inimers, polymerization conditions were optimized to avoid cross-linking and to synthesize soluble polymer in significant quantity. Not all conditions produced polymers with significant amounts of polymer. The different polymerizing conditions will give polymers with structural variations and these conditions can be changed according to the requirements.

Figure 2:
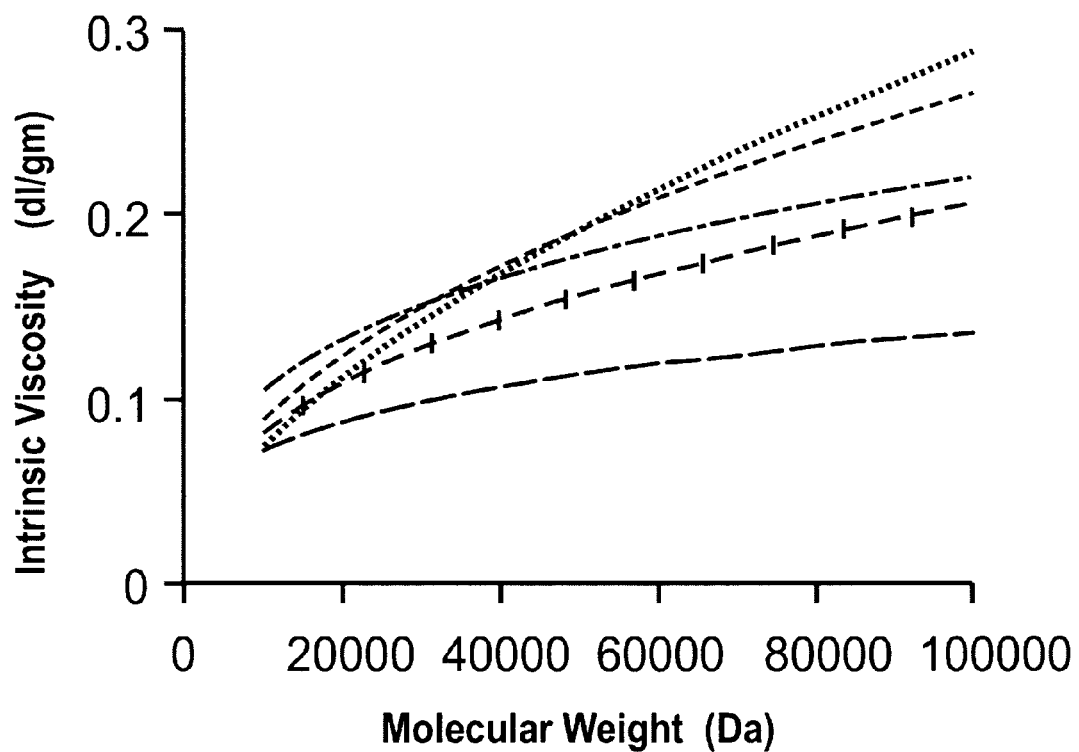
FIG. 2 is a graph of the intrinsic viscosity vs mol. wt. of mesogenic polyacrylate with different architectures.

In general, branched polymers are more compact in nature compared to the linear polymers. Contraction factor, g, which is the ratio of mean square radius of gyration of branched polymer to mean square radius of gyration of linear polymer, when extrapolated to a higher molecular weight for the different architectures provide us an idea of compactness. FIG. 2 shows that contraction factors for different architectures and also support the fact that as branching is increasing, g, is decreasing.

Figure 4:
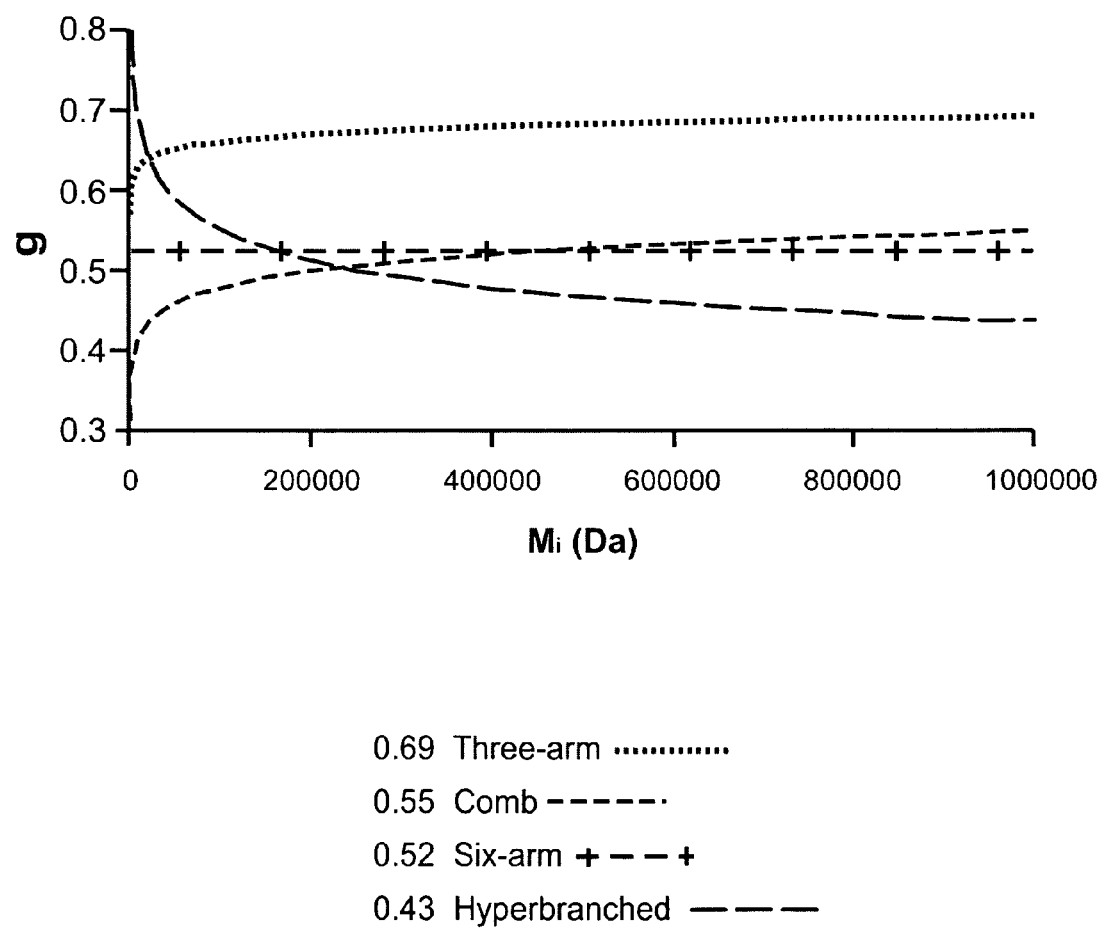
FIG. 4 is a graph of the contraction factor of different architectures of mesogenic polyacrylate.

It has been reported that hyperbranched polymers in general have lower melt or intrinsic viscosity compared to linear polymers and increasing branching in the polymer decrease the melt and intrinsic viscosity at a particular molecular weight. We have performed comparative studies on molecular weight dependent intrinsic viscosity of mesogenic polyacrylate of different architectures (linear, three-arm, six-arm, comb and hyperbranched). FIG. 4 shows that at a particular molecular weight intrinsic viscosity of the hyperbranched mesogenic polyacrylate is lower than linear mesogenic polyacrylate. It also indicates that more branched polymer have comparatively lower intrinsic viscosity than linear polymer. We have observed that at particular molecular weight intrinsic viscosity of different architectures follow a trend: Linear>Three-arm>Comb>Six-arm>Hyperbranched.

This behavior is consistent with the fact that increasing branching cause reduction in intrinsic viscosity of the polymer. This property can be utilized in many applications having processing advantages over linear polymer.

Since the polymerization of inimer could be done at different condition is resulting polymers of different degree of branching, the K and a values (from Mark-Hauwink-Sakurda equation, $\eta=KM_w{}^a$) differ. As an example: hyperbranched polymer synthesized at 120° C. in anisole as a solvent after 120 h using CuBr/PMDETA, has K=$3.365 \times 10^{-3}$ and a=0.31, while hyperbranched polymer synthesized at 90° C. in acetonitrile/water using CuBr/Me$_6$TREN, has K=$5.572 \times 10^{-3}$ and a=0.28. The linear mesogenic polyacrylate has K=$3.273 \times 10^{-4}$ and a=0.59.

As discussed earlier, mesogenic hyperbranched polyacrylate is novel since the mesogen is attached as a side chain throughout the branched structure, unlike numerous dendrimers and hyperbranched polymers with the mesogens attached only at the periphery or within the main-chain of the polymer. The mesogen containing hyperbranched polyacrylate exhibited liquid crystalline behavior. For example: a soluble mesogenic polymer with DP$_n$~20 ($M_n$=$1.30 \times 10^{-4}$) and pdi=1.56 (both values by GPC) was obtained using the ratio of 20/1/1 Inimer/Cu(I)Br/PMDETA for 10 h at 120° C. This polymer showed liquid crystallinity with isotropization transition at 99° C. in addition to a glass transition at 11° C. These transitions are at lower temperatures than those of other architectures of comparable molecular weight, and the isotropization transition was relatively broad (14° C.). The polymer formed a smectic C and a Smectic A ($S_A$) mesophases like other architectures. Thus, it is possible to make a hyperbranched liquid crystalline polymer with a mesogen attached as a free ester group in all the branches of the hyperbranched polymer. The liquid crystallinity of the hyperbranched polymer can be combined with the lower viscosity of the hyperbranched polymer and can be investigated for its use in display devices. These polymers can potentially be used alone or in combination with the lower molecular weight liquid crystals (eg: blend) in the display devices.

As noted earlier, these hyperbranched polymers can also be synthesized by copolymerizing inimers with the corresponding monomers, which may be more economical, especially in the case of costly synthesis of a large quantity of inimers. We have successfully made hyperbranched polymer by using SCVCP and ATRP. An example: mesogenic inimer [2-chloro-2-{11-(4'-cyanophenyl-4''-phenoxy)undecan-1-oxycarbonyl}]ethyl propenoate was copolymerized with 11-[(4'-cyanophenyl-4''-phenoxy)undecyl]acrylate in anisole at 130° C. for 20 h to generate soluble polymer with $M_n$=$1.03 \times 10^4$, pdi=1.22 (both values by GPC) using 20:1:1.2:1 Monomer/Inimer/Cu(I)Cl/PMDETA.

A wide variety of hyperbranched polyacrylates with different ester substituents could be polymerized by SCVP of corresponding inimers or by SCVCP with monomers. Examples: Hyperbranched poly (dodecyl acrylate) was synthesized, which might have potential applications in colloids and surface-coatings where surface of longer alkyl chains is required with lower viscosity of the polymer. Hyperbranched poly (perfluoro acrylate are potential candidates in the field of coatings. Hyperbranched poly (acrylic acid) was synthesized by SCVCP of methyl inimer (Br) and t-butyl acrylate, which was further deprotected using formic acid to obtain carboxylic acid groups in the polymer. This hyperbranched poly (acrylic acid) can be used as a superabsorbent polymer, e.g. in diapers.

The processing conditions can be varied depending upon the starting materials and inimers employed. For example, (meth)acrylic acid, (meth)acryloyl chloride or (meth)acrylic anhydride can be added as further reactants, a nucleophile/base, such as triethylamine or pyridine can optionally added, and a solvent such as tetrahydrofuran (THF) or dichloromethane can be employed. The reaction will be conducted at a temperature range of about 0° C. to ambient temperature or higher, such 50° C.

Depending upon the requirements, inimers with different ester substituents can be produced. The hyperbranched polymers resulting from these inimers having different ester groups attached as pendant groups of the polyacrylates can be used in different applications. These polymers would have lower viscosity and shear thinning behavior, which would ease their processing. Since they have a large number of end groups, which can be directly used for better interactions with the other substrates or can be modified and used. Incorporation of the different functional groups in the polymer obtained can be potentially used in wide variety of the applications from additives, surface coatings, drug delivery materials to high-tech liquid crystalline display devices. Hyperbranched polyacrylate with oligo-oxyethylene/oligo (ethylene glycol) side chains can be used in water based adhesives, in cosmetics as viscosity modifiers and in polymer electrolytes or ion-conducting polymers. Hyperbranched polyacylic acid and its salts can also be used in superabsorbent materials and in polyelectrolytes. Siloxane containing hyperbranched polyacrylates could be a potential competitor in materials for contact lenses because of higher oxygen permeability. They can also be used in hydrogels as halogen end groups in the hyperbranched polymers can be used for cross-linking sites. The halogen end groups can also be reduced to hydrogen for other applications, such as those requiring more stability. Siloxane containing inimers can also be copolymerized with hydroxy ethyl methacrylate to get the optimum oxygen permeability and water absorption. These hyperbranched polymers can also be used in fabrication of organic-inorganic hybrids and nanomaterials. Patterning of polymer films at micron or submicron level can be achieved because of functional end groups present in the hyperbranched polymer. Moities with interesting optical, biological, mechanical and electrochemical properties can be incorporated into the hyperbranched polymer films. Because of the low viscosity and abundant functional end groups, these polymers can be used in coatings, adhesives, viscosity modifiers and in packaging. Since, various desired ester group can be incorporated within the inimer, a wide variety of polyacrylates for different applications can be used.

EXAMPLES

Materials.

DL-Serine (Acros Organics, 99%), potassium bromide (Sigma-Aldrich, 99%), potassium carbonate (Riedel-De Haen, 99%), hydrogen bromide (Sigma-Aldrich, 48% aqueous solution), hydrogen chloride (EMD, GR ACS, 12M), sodium nitrite (Sigma-Aldrich, 99.5%), 11-bromo-1-undecanol (Alfa-Aeaser, 97%), 4-cyano-4'-hydroxy biphenyl (TCI, 95%), N,N,N',N'-pentamethyldiethylenetriamine (PMDETA) (Aldrich, 99%), 2,2'-dipyridyl (Lancaster Synthesis), tris(2-aminoethyl)amine (TREN) (Strem Chemicals, 97%), anisole (Aldrich, anhydrous, 99.7%), potassium hydroxide (Fisher Chemicals, certified ACS), 1H,1H,2H,2H-perfluoro-1-decanol (SynQuest), 1-dodecanol (Alfa Aesar, 98%) were used as received. Triethylamine (EM science, 98%) was stirred over KOH and distilled under $N_2$ at 80° C.-85° C. and stored over KOH. Acryloyl chloride (Aldrich, 96%) was distilled at 70° C.-75° C. and refrigerated. Benzene (Fisher Chemicals, Certified ACS) was washed with concentrated $H_2SO_4$ and vacuum distilled over $CaH_2$ and stored over 4 A° molecular sieves. Cuprous (I) chloride was purified by stirring it with glacial acetic acid overnight followed by washing several times with ethanol. Reagent grade tetrahydrofuran (THF) was dried by distillation from purple sodium benzophenone ketyl under $N_2$. All other reagents and solvents are commercially available and used as received.

Techniques.

All reactions were performed under a $N_2$ atmosphere using a Schlenk line unless noted otherwise. Elemental analyses were performed on a PE 2400 Series II CHNS/O Analyzer. $^1$H and $^{13}$C NMR spectra (δ, ppm) were recorded on either a Varian Mercury 300 (300 MHz and 75 MHz, respectively), an INOVA 400 (400 MHz and 100 MHz, respectively) or an INOVA 750 (750 MHz and 188 MHz, respectively) spectrometer. All spectra were recorded in $CDCl_3$ or a mixture of $CDCl_3$ and DMSO-$d_6$, and the resonances were measured relative to residual solvent resonances and referenced to tetramethylsilane. Number—($M_n$) and weight average ($M_w$) molecular weights relative to linear polystyrene ($GPC_{PSt}$) and polydisperisties (pdi=$M_w/M_n$) were determined by gel permeation chromatography (GPC) from calibration curves of log $M_n$ vs. elution volume at 35° C. using THF as solvent (1.0 mL/min), a set of 50 Å, 100 Å, 500 Å, $10^4$ Å and linear (50-$10^4$ Å) Styragel 5 μm columns, a Waters 486 tunable UV/Vis detector set at 254 nm, a Waters 410 differential refractometer, and Millenium Empower 2 software. Absolute molecular weights were determined by GPC with a light scattering detector ($GPC_{LS}$) at 35° C. using THF as solvent (1.0 mL/min), a set of 100 Å and two linear (50-$10^4$ Å, $10^3$-$10^6$ Å) Styragel 5 μm columns, and a Wyatt Technology DAWN-EOS 18-angle (20°-153°) light scattering detector equipped with a Ga—As laser (690 nm, 30 mW), with the concentration at each elution volume determined using a Optilab 903 differential refractometer (690 nm). The molecular weight data were calculated using Astra 4.73.04 software (Wyatt Technology). The refractive index (RI) increments (dn/dc=0.120 mL/g in $CH_2Cl_2$) were measured online at room temperature at 690 nm by Optilab 903 and used to determine the mass concentrations at each elution volume and the physical constant K* for the light scattering measurements. All samples (approximately 0.5 g/L) were dissolved overnight and filtered through a 0.45 μm PTFE filter. Molecular weights were also determined by GPC-RI-viscometry-right angle laser light scattering ($GPC_{triple}$) from universal calibration curves using $GPC_{LS}$ system combined with a Viscotek 100 differential viscometer and OmniSEC 4.3.1.246 software from Viscotek.

Molecular weight from solution viscosity measurements were obtained from universal calibration curves with application of online viscosity detector and online light scattering detector at 90°. The calculation was done using OmniSEC 4.0 software from Viscotek and chromatographic set-up used was same as for light scattering experiment.

A Perkin-Elmer Pyris 1 differential scanning calorimeter was used to determine the thermal transitions, which were read as the maximum or minimum of the endothermic and exothermic peaks, respectively. Glass transition temperature was read as the middle of the change in heat capacity. All heating and cooling rates were 10° C./min. Transition temperatures were calibrated using indium and benzophenone standards, and enthalpy changes were calibrated using indium. All samples were dried in the vacuum chamber before performing DSC experiments.

Synthesis of 2-Bromo-3-hydroxypropionic acid

2-Bromo-3-hydroxypropionic acid was synthesized in 50-63% yield as in the following example. Sodium nitrite (12 g, 0.17 mol) was added in portions over 270 min to a solution of D, L-serine (10 g, 0.10 mol), HBr (26 mL, 48% aq. w/w, 0.23 mol) and potassium bromide (40 g, 0.33 mol) in water (88 mL) at −10 to 0° C. After stirring at room temperature for 16 h, the light-greenish solution was saturated with NaCl and extracted five times with ethyl acetate (50 mL each). The combined organic extracts were washed five times with saturated aqueous NaCl (50 mL each) and dried over $Na_2SO_4$. After filtration and removing the solvent by trap-to-trap distillation, the residue was recrystallized from $CH_2Cl_2$ to obtain 10 g (63%) of 2-bromo-3-hydroxypropionic acid as a white solid. $^1$H NMR ($CDCl_3$/DMSO-$d_6$): 2.01 (broad s, OH), 3.77 (m, $CH_2OH$), 4.10 (t, CHBr), 7.20 (broad s, COOH). $^{13}$C NMR ($CDCl_3$/DMSO-$d_6$): 45.6 (CBr), 64.0 (COH), 171.0 (C=O). Anal. C, H: calcd. 21.32, 2.98; found 20.95, 2.90.

Synthesis of 2-chloro-3-hydroxypropionic acid

In a 3-necked 1000 ml. RB flask, sodium nitrite (68.4 g, 0.99 mol) was added in small batches to the aqueous solution of a mixture of DL-serine (52.4 g, 0.50 mol), potassium chloride (130.4 g, 1.75 mol) and HCl (116.0 g of 36.5%-38% w/v aq. sol., 1.21 mol) (taken together in 490 mL of water) at 0° C.-10° C. After complete addition, reaction mixture brought to room temperature and kept overnight for the reaction. Solution turned from clear and off-white to clear and light green. The product was salted out with NaCl and extracted with 5 times of 100 mL of ethyl acetate. Organic phase was washed 5 times with saturated NaCl aqueous solution (50 mL each) and then dried over anhy. $Na_2SO_4$. Solution was filtered and solvent was evaporated by trap-to-trap distillation method followed by drying in the vacuum chamber. Product was recrystallized in $CH_2Cl_2$. Yield=36.5 g (58%). $^1$H NMR ($CDCl_3$/DMSO-$d_6$): 2.01 (br s, OH), 3.98 (m, $CH_2OH$), 4.42 (t, CHCl), 7.20 (br s, COOH). $^{13}$C NMR ($CDCl_3$/DMSO-$d_6$): 57.8 (CCl), 64.3 (COH), 170.4 (C=O). Anal. C, H: calcd. 28.94, 4.04; found 28.60, 3.80.

Synthesis of Methyl 2-Bromo-3-hydroxypropionate

Methyl 2-Bromo-3-hydroxypropionate was synthesized in 68-87% yield as in the following example. A solution of 2-bromo-3-hydroxypropionic acid (6.0 g, 35 mmol) and a catalytic amount of HBr (0.2 mL, 48% aq. w/w) in methanol (50 mL, 1.2 mol) was heated at 65° C. for 21 h. Excess methanol was then removed by rotary evaporation. $CH_2Cl_2$ (100 mL) was added to the brownish liquid residue and the resulting solution was washed twice with dilute aq. $NaHCO_3$ (50 mL) and once with 50 mL of satd. NaCl aq. soln., and then dried over $Na_2SO_4$. After filtration and removing the solvent by rotary evaporation methyl 2-bromo-3-hydroxypropionate was obtained as a light yellow liquid. Product (5.7 g, 87%) as a clear liquid was obtained by purification by silica gel chromatography using $CH_2Cl_2$/ethyl ether (90/10) with $R_f$=0.31. $^1$H NMR ($CDCl_3$): 2.70 (br s, OH), 3.81 ($CH_3$), 4.00 (m, $CH_2OH$), 4.35 (t, CHBr). $^{13}$C NMR ($CDCl_3$): 44.2 (CBr), 53.5 ($CH_3$), 63.8 ($CH_2OH$), 169.7 ($CO_2CH_3$). Anal. C, H: calcd. 26.23, 3.86; found 25.83, 4.10.

Synthesis of methyl 2-chloro-3-hydroxypropionate

Methyl 2-Chloro-3-hydroxypropionate was synthesized in 68-88% yield using a procedure as in the following example. In a 250 mL RB flask with a condenser, 2-chloro-3-hydroxypropionic acid (20.0 g, 0.16 mol) and methanol (200 mL, 5.00 mol) (was dried over 4 A° molecular sieves) and a catalytic amount of hydrochloric acid were mixed and heated up to 65° C. for 22 h. Unreacted excess methanol was removed by rotary evaporation. A brownish liquid was obtained and was added with 100 mL of $CH_2Cl_2$ and washed twice with dil. $NaHCO_3$ aq. sol. (50 mL) and once with sat. aq. NaCl (50 mL) soln. and then dried over anhy. $Na_2SO_4$. Product as a clear liquid was purified by silica gel chromatography using chloroform/diethyl ether (90/10) with $R_f$=0.51, yield=17.0 g (76%). $^1$H NMR ($CDCl_3$): 2.55 (br s, OH), 3.82 ($CH_3$), 3.99 (m, $CH_2OH$), 4.41 (t, CHCl). $^{13}$C NMR ($CDCl_3$): 53.4 ($CH_3$), 57.0 (CCl), 64.2 ($CH_2OH$), 169.0 ($CO_2CH_3$). Anal. C, calcd. 34.68, 5.09; found 34.33, 4.99.

Synthesis of (3,3,4,4,5,5,6,6,7,7,8,8,9,9,10,10,10-heptadecafluoro-1-decyl)-2-chloro-3-hydroxypropionate In a 50 mL RB with a condenser, 2-chloro-3-hydroxypropionic acid (6.0 g, 0.05 mol) and 3,3,4,4,5,5,6,6,7,7,8,8,9,9,10,10,10-heptadecafluoro-1-decanol (18.0 g, 0.04 mol) and a catalytic amount of hydrochloric acid were taken together and heated up to 65° C. for 36 h. Product was dissolved in 300 mL of ethyl ether and washed twice with 100 mL of dil. $NaHCO_3$ aq. sol. and once with 100 mL of sat. aq. NaCl sol. and then dried over anhy. $Na_2SO_4$. Solution was filtered, solvent was removed by rotary evaporation and unreacted alcohol was sublimed off at 70° C. under vacuum. Yield=15.0 g (67%). $^1$H-NMR ($CDCl_3$, 7.27 ppm): 2.54 (m, —$CH_2CF_2$). 3.05-3.35 (broad, —OH), 4.01 (m, —$CH_2OH$), 4.42 (m, —CHCl), 4.52 (m, —$CO_2CH_2CH_2$).

Synthesis of 11-(4'-cyanophenyl-4"-phenoxy)undecanol

In a 3-necked (500 mL) RB flask a mixture of 4-cyano-4'-hydroxybiphenyl (10.0 g, 0.05 mol) and $K_2CO_3$ (8.5 g, 0.06 mol) were dissolved in ethanol/water (128 mL/32 mL, 80%/20% (v/v)). A solution of 11-bromo-1-undecanol (14.2 g, 0.06 mol) in ethanol (100 mL) was added dropwise to it using a pressure equalizer at room temperature. After complete addition, solution was brought to an oil bath set at 60° C. After 23 h the solution was poured into 500 mL of ice-chilled distilled water and stirred for 1.5 h. The product was filtered out using a frit and recrystallized twice in ethanol (300 mL). Final yield=8.92 g (47%). $^1$H-NMR ($CDCl_3$, 7.27 ppm): 1.31 (m, $(CH_2)_6$), 1.48 (m, —$CH_2CH_2CH_2OAr$), 1.59 (m, —$CH_2CH_2OH$), 1.82 (m, —$CH_2CH_2OAr$), 3.65 (t, —$CH_2OH$), 4.02 (t, —$CH_2OAr$), 7.00 (d, 2 aromatic H ortho to —$OCH_2$), 7.53 (d, 2 aromatic H meta to —$OCH_2$), 7.67 (m, 4 aromatic H ortho and meta to —CN).

Synthesis of {11-(4'-cyanophenyl-4"-phenoxy)undecyl}2-chloro-3-hydroxypropionate In a 50 mL RB flask, 2-chloro-3-hydroxypropionic acid (2.1 g, 0.02 mol) and 11-(4'-cyanophenyl-4"-phenoxy)undecanol (5.2 g. 0.01 mol) and a catalytic amount of hydrochloric acid were stirred and heated up to 65° C. for 42 h. $^1$H-NMR showed 20% unreacted alcohol. Product was purified by silica gel column chromatography using ether/chloroform (30/70 v/v) with $R_f$=0.77 for the product. After removing the solvent by rotary evaporation and drying in the vacuum oven, final yield=3.35 g (56%). $^1$H-NMR: 1.31 (m, $(CH_2)_6$), 1.48 (m, —$CH_2CH_2CH_2OAr$), 1.69 (m, —$CH_2CH_2OCO$), 1.82 (m, —$CH_2CH_2OAr$), 2.40 (s, broad for —OH), 4.02 (m, —$CH_2OH$ & —$CH_2OAr$), 4.21 (m, —$CO_2CH_2$), 4.36 (s, —CHCl), 7.00 (d, 2 aromatic H ortho to —$OCH_2$), 7.53 (d, 2 aromatic H meta to —$OCH_2$), 7.67 (m, 4 aromatic H ortho and meta to —CN).

Synthesis of dodecyl 2-chloro-3-hydroxypropionate 2-chloro-3-hydroxypropionic acid (4.80 g, 0.03 mol), dodecanol (6.00 g, 0.03 mol) were taken with 5 mL dry benzene in a (50 mL) RB, with a dean-stark apparatus and condenser; 25 mg (0.26 mmol) para-Toluene sulfonic acid (pTSA) was added to it and the mixture was stirred at 75° C.-80° C. for 40 h. $^1$H-NMR showed 85% conversion. More 2-chloro-3-hydroxypropionic acid (1.00 g, 8.00 mmol) was added to it and heated at 75° C.-80° C. for 20 h. $^1$H-NMR showed almost complete conversion. After cooling it down, the product was added with 100 mL of $CH_2Cl_2$. Organic phase was washed twice with 50 mL of dil. $NaHCO_3$ aq. sol. and once with 50 mL of sat. NaCl aq. sol. and then dried over anhy. $Na_2SO_4$. After filtration and removing the solvent by rotary evaporation, yield=7.76 g (78%). It was used for the next reaction without further purification. $^1$H-NMR ($CDCl_3$, 7.27 ppm): 2.18-2.40 (broad, —OH), 3.97 (m, —$CH_2OH$), 4.21 (m, —$CO_2CH_2$), 4.39 (m, —CHCl).

Synthesis of Acrylic Anhydride

Acrylic anhydride was synthesized in 70-80% yield as in the following example. Acryloyl chloride (2.7 g, 30 mmol) was added dropwise over 5 min to an ice-cooled solution of acrylic acid (2.0 g, 30 mmol) and triethylamine (2.8 g, 30 mmol) in THF (50 mL), and the solution was stirred at room temperature for 16 h. The $NH_4^+Cl^-$ precipitate was collected in a fritted glass filter, and the solvent was then removed from the filtrate by rotary evaporation. The residue was dissolved in $CH_2Cl_2$ (25 mL), washed twice with dilute aq. $NaHCO_3$ (50 mL each) and once with satd. NaCl aq. soln. (50 mL), and dried over anhy. $Na_2SO_4$. After filtration and removing the solvent by rotary evaporation, 2.8 g (80%) of acrylic anhydride was obtained as a light yellow liquid. It was used without further purification. $^1$H NMR (CDCl$_3$, 77.23 ppm): 6.04 (m, =CH trans to CO$_2$), 6.14 (m, =CH gem to CO$_2$), 6.50 (d, =CH cis to CO$_2$). $^{13}$C NMR (CDCl$_3$/DMSO-d$_6$): 127.4 (=CH), 134.7 ('CH$_2$), 161.2 (C=O).

Synthesis of (2-Bromo-2-methoxycarbonyl)ethyl propenoate (2-Bromo-2-methoxycarbonyl)ethyl propenoate was synthesized in 55-68% (68%) yield as in the following example. A solution of acrylic anhydride (0.80 g, 6.3 mmol) in THF (5 mL) was added dropwise over 10 min to a solution of methyl 2-bromo-3-hydroxypropionate (0.50 g, 2.7 mmol) and triethylamine (0.55 g, 5.4 mmol) in THF (25 mL) at room temperature. After stifling at RT for 21 h, the solution was poured into ice-cooled water (25 mL) and stirred for 3 h. THF was removed by rotary evaporation and CH$_2$Cl$_2$ was added. After separating the two layers, the organic phase was washed twice with dil. aq. NaHCO$_3$ (25 mL each) and once with satd. NaCl aq. soln. (25 mL), and dried over Na$_2$SO$_4$. After filtration and removing the solvent by rotary evaporation (2-bromo-2-methoxycarbonyl)ethyl propenoate was obtained as a yellow liquid. Pure product as a clear liquid (0.44 g, 68%) was obtained by vacuum distillation at full vacuum at 92-94° C. $^1$H NMR (CDCl$_3$, 7.27 ppm): 3.83 (s, CH$_3$), 4.58 (m, CO$_2$CH$_2$ & CHBr), 5.92 (dd, =CH trans to CO$_2$), 6.14 (dd, =CHCO$_2$), 6.43 (dd, =CH cis to CO$_2$). $^{13}$C NMR (CDCl$_3$, 77.23 ppm): 40.4 (CBr), 53.5 (CH$_3$), 64.31 (CH$_2$O$_2$C), 127.6 (=CH), 132.4 (=CH$_2$), 165.3 (CO$_2$CH$_3$), 168.3 (CO$_2$CH$_2$). Anal. C, H: calcd. 35.47, 3.83; found 35.24, 3.75.

Synthesis of (2-Chloro-2-methoxycarbonyl)ethyl propenoate (2-Chloro-2-methoxycarbonyl)ethyl propenoate was synthesized in 34-50% (34%) yield using the same procedure as above, except that methyl 2-chloro-3-hydroxypropionate was used instead of methyl 2-bromo-3-hydroxypropionate. Pure product as a clear liquid was obtained by vacuum distillation at full vacuum at 94-96° C. $^1$H NMR (CDCl$_3$, 7.27 ppm): 3.79 (s, CH$_3$), 4.52 (m, CO$_2$CH$_2$ & CHCl), 5.88 (dd, =CH trans to CO$_2$), 6.11 (dd, =CHCO$_2$), 6.44 (dd, =CH cis to CO$_2$). $^{13}$C NMR (CDCl$_3$, 77.23 ppm): 53.5 (CH$_3$), 53.7 (CCl), 64.6 (CH$_2$O$_2$C), 127.6 (=CH$_2$), 132.3 (=CH), 165.4 (CO$_2$CH$_3$), 167.9 (CO$_2$CH$_2$). Anal. C, H: calcd. 43.65, 4.71; found 43.48, 4.73.

Synthesis of {2-chloro-2-(3,3,4,4,5,5,6,6,7,7,8,8,9,9,10,10,10-heptadecafluorodecan-1-oxycarbonyl)}ethyl propenoate In a 3-necked RB flask (250 mL), a solution of triethylamine (1.80 g, 0.02 mol) in THF (5 mL) was added dropwise to the ice-cooled solution of (3,3,4,4,5,5,6,6,7,7,8,8,9,9,10,10,10-heptadecafluoro-1-decyl)-2-chloro-3-hydroxypropionate (5.00 g, 0.01 mol) and acryloyl chloride (1.54 g, 0.02 mol) in THF (80 mL). The solution was brought to ambient temperature for the further reaction. After 12 h, reaction was stopped by pouring solution into ice cooled water (100 mL) and was stirred overnight. Aqueous phase was added with CH$_2$Cl$_2$ (100 mL) and water phase was neutralized with addition of a small amount of NaHCO$_3$. Product was extracted by washing water phase with 5 times of CH$_2$Cl$_2$ (50 mL). Combined organic phase was washed twice with 50 mL of dil. NaHCO$_3$ aq. sol. and once with 50 mL of sat. NaCl aq. sol. and then dried over anhy. Na$_2$SO$_4$. Product was purified by a silica gel column chromatography using CHCl$_3$ as an eluting solvent with R$_f$=0.61-0.74. Yield=2.37 g (43%). $^1$H-NMR (CDCl$_3$, 7.27 ppm): 2.52 (m, —CH$_2$CF$_2$), 4.55 (m, —CO$_2$CH$_2$CH, —CHCl & —CO$_2$CH$_2$CH$_2$), 5.89 (dd, 1 olefinic H trans to —CO$_2$), 6.12 (dd, 1 olefinic H gem to —CO$_2$), 6.41 (dd, 1 olefinic H cis to —CO$_2$). $^{13}$C-NMR (CDCl$_3$, 77.23 ppm): 30.5 (—CH$_2$CF$_2$), 53.4 (—CHCl), 58.4 (—OCH$_2$CH$_2$), 64.4 (—OCH$_2$CHCl), 105.0-122.0 ((CF$_2$)$_7$ & —CF$_3$), 127.5 (vinylic CH), 132.3 (vinylic CH$_2$), 165.4 (—CO$_2$CH$_2$CHCl), 167.2 (—CO$_2$CH$_2$CH$_2$). Anal. C, H: calcd. 30.76, 1.71; found 30.84, 1.55.

Synthesis of [2-chloro-2-{11-(4'-cyanophenyl-4"-phenoxy)undecan-1-oxycarbonyl}]ethyl propenoate In a 3 necked RB flask (50 mL), a solution of triethylamine (2.15 g. 0.02 mol) in THF (3 mL) was added dropwise to the ice-cooled solution of {11-(4'-cyanophenyl-4"-phenoxy)undecyl}2-chloro-3-hydroxypropionate (3.20 g, 6.7 mmol) in THF (25 mL), which was followed by the dropwise addition of a solution of acryloyl chloride (1.88 g, 0.02 mol) in THF (3 mL). After 9 h, reaction was stopped by pouring solution into ice cooled water (50 mL) and was stirred overnight. Aqueous phase was added with chloroform (50 mL) and water phase was neutralized with addition of a small amount of NaHCO$_3$. Product was further extracted by washing water phase with 2 times of chloroform (50 mL). Organic phase was washed with dil. NaHCO$_3$ aq. sol. and dried over anhy. Na$_2$SO$_4$. Solution was filtered and solvent was removed by rotary evaporation. Product was purified by silica gel chromatography using ether/chloroform (5%/95%) as an eluting solvent mixture, R$_f$=0.70. After removing solvent, and drying, yield=2.16 g (61%). Product was recrystallized in ethanol. After filtration and drying in the vacuum oven, yield=1.36 g (38%). $^1$H-NMR (CDCl$_3$, 7.27 ppm): 1.31 (m, (CH$_2$)$_6$), 1.48 (m, —CH$_2$CH$_2$CH$_2$OAr), 1.69 (m, —CH$_2$CH$_2$OAr), 1.82 (m, —CH$_2$CH$_2$OCO), 4.01 (t, —CH$_2$OAr), 4.20 (t, —CH$_2$O$_2$C), 4.54 (m, —CHCl & —CO$_2$CH$_2$CHCl), 5.90 (dd, 1 olefinic H trans to —CO$_2$), 6.15 (dd, 1 olefinic H gem to —CO$_2$), 6.46 (dd, 1 olefinic H cis to —CO$_2$), 6.99 (d, 2 aromatic H ortho to OCH$_2$), 7.67 (m, 4 aromatic H ortho and meta to —CN), 7.53 (d, 2 aromatic H meta to OCH$_2$). $^{13}$C-NMR (CDCl$_3$, 77.23 ppm): 25.9-29.7 ((CH$_2$)$_9$), 53.9 (CHCl), 64.7 (—OCH$_2$(CH$_2$)$_{10}$), 66.8 (—OCH$_2$CHCl), 68.4 (—CH$_2$OAr), 110.2 (aromatic C adjacent to —CN), 115.3 (aromatic C ortho to O), 119.3 (—CN), 127.3 (aromatic C meta to CN), 127.6 (vinylic CH), 128.5 (aromatic C meta to O), 131.4 (aromatic C para to O), 132.3 (vinylic CH$_2$), 132.8 (aromatic C ortho to —CN), 145.5 (aromatic C para to —CN), 160.0 (aromatic C adjacent to O), 165.4 (—CO$_2$CH$_2$CHCl), 167.4 (—CO$_2$(CH$_2$)$_{11}$). Anal. C, H, N: calcd. 68.49, 6.90, 2.66; found 68.24, 6.88, 2.93.

Synthesis of (2-chloro-2-dodecan-1-oxycarbonyl)ethyl propenoate

In a 3 necked 100 mL RB flask, a solution of acryloyl chloride (1.95 g, 21.5 mmol) in 5 mL THF was added dropwise to a solution of dodecyl 2-chloro-3-hydroxypropionate (4.20 g, 14.3 mmol) and triethylamine (2.17 g, 21.5 mmol) in 50 mL dry THF at 0° C. After complete addition, RB was brought to ambient temperature and stirred for 21 h. Reaction was stopped by pouring the solution into ice-chilled water (100 mL) and stirred overnight to evaporate THF. Product was extracted by washing aqueous phase 5 times with 50 mL of CH$_2$Cl$_2$. The organic phase was washed twice with 50 mL of dil. NaHCO$_3$ aq. sol. and once with 50 mL of sat. NaCl aq. sol. The organic phase was dried over anhy. Na$_2$SO$_4$. After filtration, the solvent was removed by rotary evaporation. The product was purified silica gel column chromatography using ethyl acetate (1-5%)/hexane solvent mixture as an eluting medium. Yield=2.92 g (59%). $^1$H-NMR (CDCl$_3$, 7.27 ppm): 0.84 (t, CH$_3$), 1.10-1.38 (m, (CH$_2$)$_9$), 1.62 (m, —CH$_2$(CH$_2$)$_9$CH$_3$), 4.18 (m, —CO$_2$CH$_2$CH$_2$), 4.54 (m, —CO$_2$CH$_2$CHCl, —CHCl), 5.86 (d, olefinic H trans to CO$_2$), 6.10 (dd, H gem to CO$_2$), 6.45 (d, olefinic H cis to CO$_2$). $^{13}$C-NMR (CDCl$_3$, 77.23 ppm): 14.1 (CH$_3$), 22.4-31.8 ((CH$_2$)$_9$), 53.9 (—CHCl), 66.8 (—OCH$_2$CHCl), 127.7 (vinylic CH), 132.1 (vinylic CH$_2$), 165.2 (—CO$_2$CH$_2$CHCl), 167.6 (—CO$_2$(CH$_2$)$_{11}$CH$_3$). Anal. C, H: calcd. 62.32, 9.01; found 62.19, 9.36.

Synthesis of Tris(2-(dimethylamino)ethyl)amine (Me$_6$TREN)

In a 250 mL round bottom flask TREN (10.00 g, 0.07 mol) in water (25 mL) was added dropwise using a pressure equalizer to an ice chilled mixture of formaldehyde (36% in water) (39.00 g, 0.47 mol) and formic acid (55.16 g, 1.2 mol). After complete addition of TREN, the RB was brought to an oil bath and the solution was refluxed gently overnight at 100° C. It was cooled to room temperature and water was removed by trap-to-trap distillation. To remove unreacted formic acid, product was dissolved in 20 mL of acetonitrile and passed through a basic alumina column. Acetonitrile was removed by rotary evaporation and product was further purified by vacuum distillation. Yield=4.10 g (26%). $^1$H-NMR (CDCl$_3$, 7.27 ppm): 2.22 (s, —CH$_3$), 2.37 (dd, —CH$_2$N(CH$_2$)$_2$), 2.60 (dd, —CH$_2$N(CH$_3$)$_2$). $^{13}$C-NMR (CDCl$_3$, 77.23 ppm): 46.1 (—CH$_3$), 53.3 (—CH$_2$N(CH$_2$)$_2$), 57.7 (—CH$_2$N(CH$_3$)$_2$).

Synthesis of [11-(4'-cyanophenyl-4"-phenoxy)undecyl]acrylate

In a 250 mL 3-necked RB, a solution of triethylamine (0.42 g, 4.18 mmol) in THF (10 mL) was added dropwise to the ice-cooled solution of 11-(4'-cyanophenyl-4"-phenoxy)undecanol (0.91 g, 2.5 mmol) in THF (200 mL), which was followed by the dropwise addition of a solution of acryloyl chloride (0.33 g, 3.65 mmol) in THF (10 mL). After 18 h, reaction was stopped by pouring solution into ice cooled water (200 mL) and was stirred overnight to evaporate THF. Product was filtered out using a frit and dried. It was recrystallized in ethanol/toluene (50 mL/3 mL). After drying in the vacuum chamber, yield=0.87 g (84%). $^1$H-NMR (CDCl$_3$, 7.27 ppm): 1.31 (m, (CH$_2$)$_6$), 1.48 (m, —CH$_2$CH$_2$CH$_2$OAr), 1.67 (m, —CH$_2$CH$_2$OAr), 1.82 (m, —CH$_2$CH$_2$OCO), 4.00 (t, —CH$_2$OAr), 4.15 (t, —CH$_2$O$_2$C), 5.81 (dd, 1 olefinic H trans to CO$_2$), 6.10 (dd, 1 olefinic H gem to CO$_2$), 6.40 (dd, 1 olefinic H cis to CO$_2$), 7.00 (d, 2 aromatic H ortho to —OCH$_2$), 7.53 (d, 2 aromatic H meta to —OCH$_2$), 7.67 (m, 4 aromatic H ortho and meta to —CN).

Synthesis of [2-chloro-2-{11-(4'-cyanophenyl-4"-phenoxy)undecan-1-oxycarbonyl}]ethyl propen-2-meth-oate In a 3 necked RB flask (250 mL), a solution of methacryloyl chloride (0.67 g, 6.41 mmol) in THF (5 mL) was added dropwise to the ice-cooled solution of {11-(4'-cyanophenyl-4"-phenoxy)undecyl}2-chloro-3-hydroxypropionate (2.0 g, 0.42 mmol) in THF (100 mL) and triethylamine (0.65 g, 6.42 mmol). After 16 h, reaction was stopped by pouring solution into ice cooled water (200 mL) and was stirred overnight. White residual in water was filtered out and dried in the vacuum chamber. Product was purified by silica gel chromatography using ether/chloroform (5%/95%) as an eluting solvent mixture, R$_f$=0.79. After removing solvent, and drying, yield=1.63 g (71%). Product was recrystallized in ethanol, final yield=1.58 (69%). $^1$H-NMR (CDCl$_3$, 7.27 ppm): 1.30 (m, (CH$_2$)$_6$), 1.48 (m, —CH$_2$CH$_2$CH$_2$OAr), 1.66 (m, —CH$_2$CH$_2$OAr), 1.82 (m, —CH$_2$CH$_2$OCO), 1.95 (s, —CH$_3$), 4.01 (t, —CH$_2$OAr), 4.21 (t, —CH$_2$O$_2$C), 4.54 (m, —CHCl & —CO$_2$CH$_2$CHCl), 5.63 (dd, olefinic H trans to —CO$_2$), 6.15 (dd, 1 olefinic H cis to —CO$_2$), 7.00 (d. 2 aromatic H ortho to OCH$_2$), 7.53 (d, 2 aromatic H meta to OCH$_2$), 7.67 (m, 4 aromatic H ortho and meta to —CN). $^{13}$C-NMR (CDCl$_3$, 77.23 ppm): 18.4 (CH$_3$), 25.9-29.7 ((CH$_2$)$_9$), 54.0 (CHCl), 64.9 (—OCH$_2$(CH$_2$)$_{10}$), 66.8 (—OCH$_2$CHCl), 68.3 (—CH$_2$OAr). 110.2 (aromatic C adjacent to —CN), 115.3 (aromatic C ortho to O), 119.3 (—CN), 126.9 (aromatic C meta to CN), 127.2 (vinylic CH), 128.5 (aromatic C meta to O), 131.4 (aromatic C para to O), 132.4 (vinylic CH$_2$), 132.7 (aromatic C ortho to —CN), 145.5 (aromatic C para to —CN), 160.0 (aromatic C adjacent to O), 166.6 (—CO$_2$CH$_2$CHCl), 167.5 (—CO$_2$(CH$_2$)$_{11}$). Anal. C, H, N: calcd. 68.94, 7.09, 2.59; found 68.49, 7.20, 2.42.

Polymerization of [2-chloro-2-{11-(4'-cyanophenyl-4"-phenoxy)undecan-1-oxycarbonyl}]ethyl propen-2-meth-oate by ATRP In a schlenk tube, Cu(I)Br and PMDETA were taken and stirred together under N$_2$. Anisole was added to it and stirred for 10 min followed by addition of inimer. The schlenk tube was sealed with a glass stopper and the solution was stirred for some time, a homogeneous solution was obtained. After 3 cycles of freeze-pump-thaw tube was brought to an oil bath set at 120° C. After 100 h the tube was quenched into liq N$_2$, thawed and aerated; a viscous solution was obtained. THF (5 mL) was added to it and precipitated thrice into methanol (25 mL). A light brown solid was obtained. After drying in the vacuum chamber, yield=0.42 g (70%). GPC$_{PSt}$ (THF): M$_n$=17.5×10$^3$, Pdi=2.82.

Atom Transfer Radical Polymerization of inimer. Example: Polymerization of (2-chloro-2-methoxycarbonyl)ethyl propenoate In a dried schlenk tube with a stir-bar, Cu(I)Cl (3.1 mg, 0.03 mmol) and Me$_6$TREN (6.7 mg, 0.03 mmol) were taken and stirred together under N$_2$. (2-chloro-2-methoxycarbonyl) ethyl propenoate (0.30 g, 1.55 mmol) in water as a solvent (0.30 g) was added to it and stirred for sometime under N$_2$. After 3 cycles of freeze-pump-thaw and backfilling with N$_2$ (10-30-20-10 min) schlenk tube was brought to an oil bath set at 50° C. After 44 h, reaction was stopped by quenching the tube into liquid N$_2$. It was followed by a thaw and the tube was opened to ambient atmosphere. The solution was added with 5 mL of THF and precipitated twice into 25 mL of sat. NH$_4$Cl aq. sol. followed by once into 25 mL of methanol. The product was collected and dried in vacuum chamber. A light yellow paste was obtained. Yield=0.12 g (40%). GPC$_{PSt}$ (THF): M$_n$=1.76×10$^4$, Pdi=1.52.

Atom Transfer Radical Co-polymerization of inimer with monomer. Example: Co-polymerization of [2-chloro-2-{11-(4'-cyanophenyl-4"-phenoxy)undecan-1-oxycarbonyl}]ethyl propenoate and 11-(4'-cyanophenyl-4"-phenoxy)undecyl acrylate In a dried schlenk tube with a stir-bar, Cu(I)Cl (4.1 mg, 0.04 mmol) and PMDETA (6.25 mg, 0.04 mmol) were taken and stirred together under $N_2$. Mixture of [2-chloro-2-{11-(4'-cyanophenyl-4"-phenoxy)undecan-1-oxycarbonyl}]ethyl propenoate (0.02 g, 0.04 mmol) and 11-(4'-cyanophenyl-4"-phenoxy)undecyl acrylate (0.30 g, 0.72 mmol) was added to followed by addition of anisole as a solvent (0.6 mL). The solution was stirred for 15 min. under $N_2$. After 5 cycles of freeze-pump-thaw (10-30-20 min), schlenk tube was brought to an oil bath set at 130° C. After 18 h, reaction was stopped by quenching the tube into liquid $N_2$. It was followed by a thaw and the tube was opened to ambient atmosphere. The solution was added with 5 mL of THF and precipitated twice into 25 mL of sat. $NH_4Cl$ aq. sol. followed by once into 25 mL of methanol. The product was collected and dried in vacuum chamber. A white solid was obtained. Yield=0.10 g (30%). $GPC_{PSt}$ (THF): $M_n=1.03\times10^4$, Pdi=1.22.

Atom Transfer Radical Polymerization of Inimer.
Example: Polymerization of [2-chloro-2-{11-(4'-cyanophenyl-4"-phenoxy)undecan-1-oxycarbonyl}] ethyl propenoate In a dried schlenk tube with a stir-bar, Cu(I)Cl (1.00 mg, 0.01 mmol) and $Me_6$TREN (2.1 mg, 0.01 mmol) were taken and stirred together under $N_2$. [2-chloro-2-{11-(4'-cyanophenyl-4"-phenoxy)undecan-1-oxycarbonyl}]ethyl propenoate (0.20 g, 0.34 mmol) was added to followed by addition of acetonitrile/water (0.50 mL/0.10 mL) as a solvent mixture. The solution was stirred for 15 min. under $N_2$. After 5 cycles of freeze-pump-thaw (10-30-20 min), schlenk tube was brought to an oil bath set at 90° C. After 120 h, reaction was stopped by quenching the tube into liquid $N_2$. It was followed by a thaw and the tube was opened to ambient atmosphere. The solution was added with 5 mL of THF and precipitated twice into 25 mL of sat. $NH_4Cl$ aq. sol. followed by once into 25 mL of methanol. The product was collected and dried in vacuum chamber. A white solid was obtained. Yield=0.12 g (66%). $GPC_{PSt}$ (THF): $M_n=3.26\times10^4$, Pdi=1.90.

Copolymerization of Methyl Inimer (Br) with t-Butyl Acrylate by ATRP.

In a schlenk tube, Cu(I)Br and 2,2'-dipyridyl were taken and stirred under together under $N_2$. Methyl inimer (Br) and t-butyl acrylate were mixed and added together to the schlenk tube. The tube was sealed with a glass stopper and the solution was stirred for 10 min and a homogeneous solution was obtained. After 3 cycles of freeze-pump-thaw tube was brought to an oil bath set at 90° C. After 4 h the tube was quenched into liq $N_2$, thawed and aerated; a viscous solution was obtained. THF (5 mL) was added to it and precipitated thrice into methanol/water mixture (60 mL/30 mL). A white paste was obtained. After drying in the vacuum chamber, yield=1.08 g (46%). $GPC_{PSt}$ (THF): $M_n=15.3\times10^3$, Pdi=8.84.

Deprotection of t-Butyl Group(Synthesis of Hyperbranched Acrylic Acid).

In an RB (50 mL), 0.5 gm hyperbranched poly (t-butyl acrylate) was dissolved in excess of formic acid (10 mL) and stirred at 30° C. for 24 h. Solution was concentrated and dissolved in methanol (5 mL) and precipitated in hexanes (20 mL) thrice. A light brown paste was obtained. After drying in the vacuum chamber, yield=0.18 g (67%). $GPC_{PSt}$ (DMF): $M_n=2.25\times10^5$, Pdi=10.5.

Reduction of —Cl End Group into —H (Using Tri n-Butyl Tin Hydride).

In a schlenk tube Cu(I)Br (4.4 mg, 0.037 mmol) and $Me_6$TREN (7.2 mg, 0.037 mmol) were mixed together under $N_2$. Anisole (5 mL) was added to the tube followed by addition of the hyperbranched polymer (0.16 g) ($GPC_{PSt}$ $M_n=13.0\times10^3$, Pdi=1.40). The solution was stirred for some time till the entire polymer dissolved in the solution, which was followed by the addition of tri n-butyl tin hydride (0.10 g). The schlenk tube was sealed with a glass stopper and after 3 cycles of freeze-pump-thaw, it was brought to an oil bath set at 120° C. After 5 h of the reaction, schlenk tube was quenched into liquid $N_2$, thawed and then it was opened to air. Solution was diluted with THF (5 mL), passed through a plug of basic alumina and then precipitated into methanol (50 mL) thrice. After drying in the vacuum chamber overnight, yield=0.13 g (86%). $^{13}C$ NMR showed no residual CO resonance. $GPC_{PSt}$ (THF): $M_n=9.90\times10^3$, Pdi=1.35.

Although the invention has been described in detail with reference to particular examples and embodiments, the examples and embodiments contained herein are merely illustrative and are not an exhaustive list. Variations and modifications of the present invention will readily occur to those skilled in the art. The present invention includes all such modifications and equivalents. The claims alone are intended to set forth the limits of the present invention.

The invention claimed is:

1. An inimer having the following formula

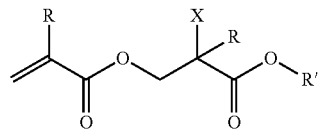

wherein X is a halogen; R is selected from the group consisting of H and CH3; and R' is selected from the group consisting of a non-hydrocarbon and a hydrocarbon,
wherein the hydrocarbon can be a linear or branched hydrocarbon or aromatic, and
wherein the non-hydrocarbon is selected from the group consisting of a fluorocarbon and (oligo)oxyethylene and siloxane substituents.

2. The inimer of claim 1, wherein X equals Br and the inimer is derived from (meth)arylic anhydride or (meth)acrylic acid.

3. The inimer of claim 1, wherein X equals Cl and the inimer is derived from (meth)acryloyl chloride or (meth)acrylic acid.

4. The inimer of claim 1, wherein R' equals an alkyl or aryl group.

* * * * *